United States Patent [19]
Andrews et al.

[11] Patent Number: 6,043,880
[45] Date of Patent: Mar. 28, 2000

[54] AUTOMATED OPTICAL READER FOR NUCLEIC ACID ASSAYS

[75] Inventors: Jeffrey P. Andrews, Abingdon; Christian V. O'Keefe, Linthicum; Brian G. Scrivens, Colora, all of Md.; Willard C. Pope, York, Pa.; Timothy Hansen, Spring Grove, Pa.; Frank L. Failing, Lewisberry, Pa.

[73] Assignee: Becton Dickinson and Company, Franklin Lakes, N.J.

[21] Appl. No.: 08/929,895

[22] Filed: Sep. 15, 1997

[51] Int. Cl.⁷ .............................. G01N 21/76; G01J 3/30
[52] U.S. Cl. .................... 356/311; 356/417; 356/246; 250/361 C; 422/52
[58] Field of Search ...................... 356/246, 417, 356/311, 437; 422/52, 65; 250/361 C

[56] References Cited

U.S. PATENT DOCUMENTS

| | | |
|---|---|---|
| 3,533,744 | 10/1970 | Unger . |
| 3,627,431 | 12/1971 | Komarniski . |
| 3,773,426 | 11/1973 | Mudd . |
| 3,792,276 | 2/1974 | Toman et al. . |
| 3,844,428 | 10/1974 | Olsen . |
| 3,852,599 | 12/1974 | Smith . |
| 3,857,485 | 12/1974 | Frank . |
| 3,883,742 | 5/1975 | Olson et al. . |
| 3,885,879 | 5/1975 | Louder et al. . |
| 3,890,505 | 6/1975 | Olson . |
| 3,898,457 | 8/1975 | Packard et al. . |
| 3,899,673 | 8/1975 | Packard . |
| 3,924,128 | 12/1975 | Frank . |
| 3,926,323 | 12/1975 | Frank et al. . |
| 3,972,778 | 8/1976 | Cunningham . |
| 4,002,909 | 1/1977 | Packard et al. . |
| 4,004,150 | 1/1977 | Natelson . |
| 4,115,010 | 9/1978 | McAleer et al. . |
| 4,147,250 | 4/1979 | Schulz . |
| 4,201,478 | 5/1980 | Gerlier et al. . |
| 4,240,751 | 12/1980 | Linnecke et al. . |
| 4,259,290 | 3/1981 | Suovaniemi et al. . |
| 4,343,991 | 8/1982 | Fujiwara et al. . |
| 4,349,510 | 9/1982 | Kolehmainen et al. . |
| 4,358,203 | 11/1982 | Citrin . |
| 4,431,307 | 2/1984 | Suovaniemi . |
| 4,465,938 | 8/1984 | Kato et al. . |
| 4,472,352 | 9/1984 | Quesneau et al. . |

(List continued on next page.)

FOREIGN PATENT DOCUMENTS

| | | |
|---|---|---|
| 0640828 | 8/1994 | European Pat. Off. . |
| 9316194 | 8/1993 | WIPO . |

OTHER PUBLICATIONS

Bactec ® 9120/9240 Brochure, Becton Dickinson and Company, 1993.
Bactec ® 9240 Brochure, Becton Dickinson and Company, 1993.
FLUOstar Microplate Fluorometer, BMG Lab Technologies GmBH, Oct. 1995.
CytoFluor II Multi–Well Fluorescence Plate Readers, Per–Septive BioSystems, 1996.
fmax Fluorescence Microplate System, Molecular Devices, 1996.
SPECTRAmax 340 Tunable Microplate Reader, Molecular Devices, 1997.

*Primary Examiner*—Frank G. Font
*Assistant Examiner*—Zandra U. Smith
*Attorney, Agent, or Firm*—David W. Highet, Esq.

[57] ABSTRACT

An apparatus and method employing a plurality of light emitting devices which each can get light through a respective optical fiber toward a respective fluid sample of a plurality of fluid samples in a time-staggered manner. Light is generated in each of the fluid samples at different times consistent with the times at which light is irradiate onto the sample. A single detector is used to detect the lights emitted from the plurality of samples at these different times. A plurality of bifurcated optical cable are coupled to the light emitting devices and single light detecting device, and the integrated end of each bifurcated cable acts as the light emitting port and light detecting port.

24 Claims, 26 Drawing Sheets

6,043,880
Page 2

U.S. PATENT DOCUMENTS

| | | |
|---|---|---|
| 4,498,780 | 2/1985 | Banno et al. . |
| 4,498,782 | 2/1985 | Proctor et al. . |
| 4,626,684 | 12/1986 | Landa ..................................... 356/318 |
| 4,651,006 | 3/1987 | Valenta . |
| 4,672,200 | 6/1987 | Claypool et al. . |
| 4,722,606 | 2/1988 | Bonfiglio et al. . |
| 4,727,033 | 2/1988 | Hijikata et al. . |
| 4,730,921 | 3/1988 | Klein et al. . |
| 4,737,464 | 4/1988 | McConnell et al. . |
| 4,762,420 | 8/1988 | Bowley . |
| 4,772,453 | 9/1988 | Lisenbee . |
| 4,778,763 | 10/1988 | Makiguchi et al. . |
| 4,844,887 | 7/1989 | Galle et al. . |
| 4,892,409 | 1/1990 | Smith . |
| 4,896,963 | 1/1990 | Kato . |
| 4,929,828 | 5/1990 | Claypool . |
| 4,940,332 | 7/1990 | Miwa et al. . |
| 4,968,148 | 11/1990 | Chow et al. . |
| 5,073,029 | 12/1991 | Eberly et al. . |
| 5,075,077 | 12/1991 | Durley, III et al. . |
| 5,112,134 | 5/1992 | Chow et al. . |
| 5,126,276 | 6/1992 | Fish et al. . |
| 5,139,745 | 8/1992 | Barr et al. . |
| 5,144,136 | 9/1992 | Kubisiak . |
| 5,146,093 | 9/1992 | Valenta et al. . |
| 5,169,601 | 12/1992 | Ohta et al. . |
| 5,173,741 | 12/1992 | Wakatake . |
| 5,192,692 | 3/1993 | Sakai et al. . |
| 5,198,670 | 3/1993 | VanCauter et al. . |
| 5,202,091 | 4/1993 | Lisenbee . |
| 5,216,488 | 6/1993 | Tuunanen et al. . |
| 5,234,665 | 8/1993 | Ohta et al. . |
| 5,270,210 | 12/1993 | Weyrauch et al. . |
| 5,281,394 | 1/1994 | Holub . |
| 5,281,540 | 1/1994 | Merkh et al. . |
| 5,298,753 | 3/1994 | Soone et al. . |
| 5,304,492 | 4/1994 | Klinkhammer . |
| 5,307,144 | 4/1994 | Hiroshi et al. . |
| 5,314,825 | 5/1994 | Weyrauch et al. . |
| 5,319,436 | 6/1994 | Manns et al. . |
| 5,320,808 | 6/1994 | Holen et al. . |
| 5,324,635 | 6/1994 | Kawase et al. . |
| 5,325,295 | 6/1994 | Fratantoni et al. . |
| 5,376,313 | 12/1994 | Kanewake, III et al. . |
| 5,407,638 | 4/1995 | Wang . |
| 5,445,794 | 8/1995 | Wihlborg . |
| 5,447,687 | 9/1995 | Lewis et al. . |
| 5,457,527 | 10/1995 | Manns et al. . |
| 5,468,453 | 11/1995 | Holt et al. . |
| 5,473,437 | 12/1995 | Blumenfeld et al. . |
| 5,482,861 | 1/1996 | Clark et al. . |
| 5,483,347 | 1/1996 | Hollman . |
| 5,490,971 | 2/1996 | Gifford et al. . |
| 5,500,188 | 3/1996 | Hafeman et al. . |
| 5,508,200 | 4/1996 | Tiffany et al. . |
| 5,516,490 | 5/1996 | Sanadi . |
| 5,518,923 | 5/1996 | Berndt et al. . |
| 5,538,849 | 7/1996 | Uematsu et al. . |
| 5,589,351 | 12/1996 | Harootunian ............................. 435/29 |
| 5,604,101 | 2/1997 | Hanley et al. . |
| 5,604,130 | 2/1997 | Warner et al. . |
| 5,611,994 | 3/1997 | Bailey et al. ........................... 422/52- |

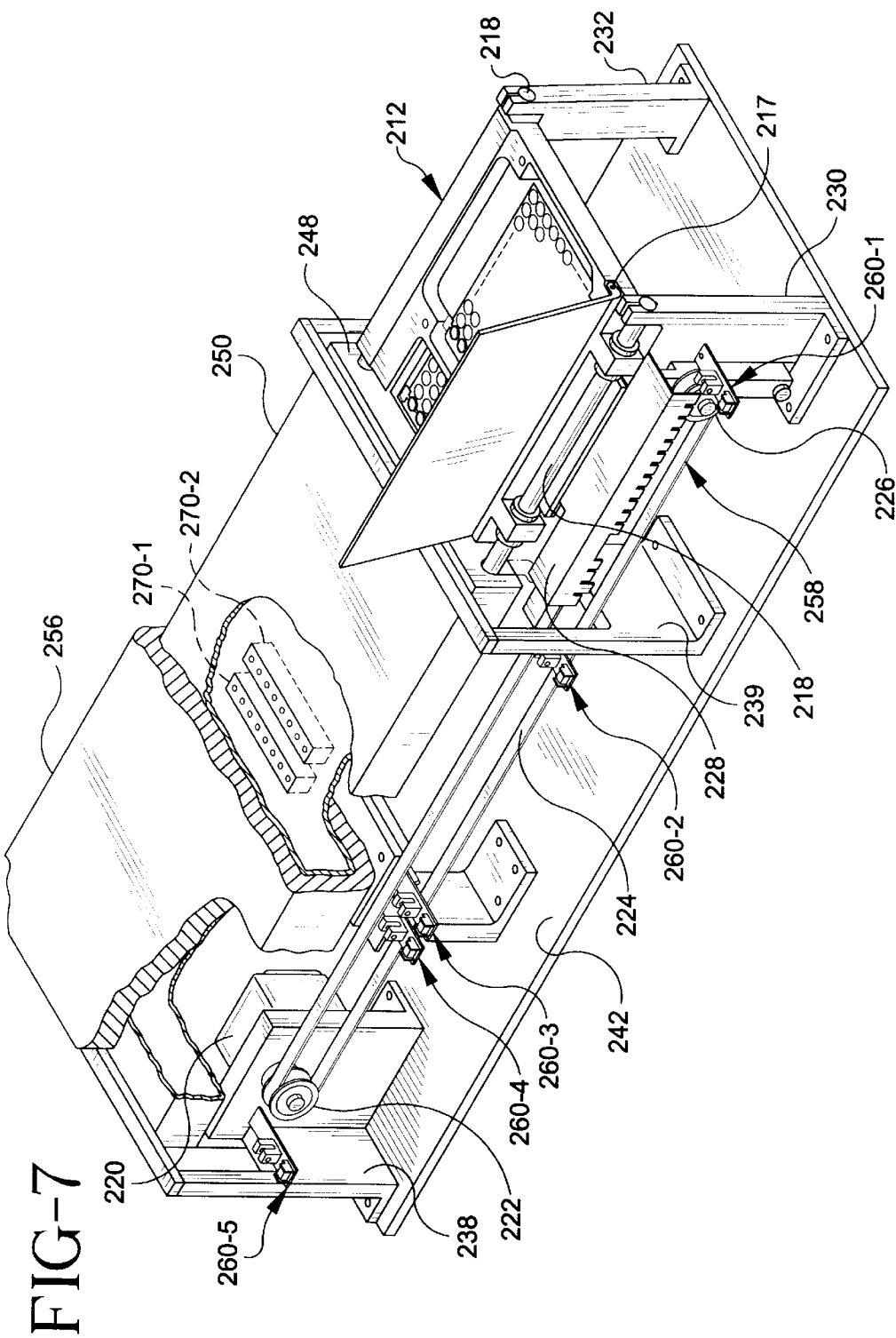

AUTOMATED OPTICAL READER FOR NUCLEIC ACID ASSAYS

FIELD OF THE INVENTION

The present invention relates to an apparatus and method for optically reading a plurality of samples in a biological or chemical assay, such as a nucleic acid assay. More particularly, the present invention relates to an apparatus and method which controls a plurality of light sources to excite a plurality of samples with light in a time-staggered fashion to cause each of the samples to fluoresce at different times, and a single detector to detect the light emitted from each of the samples.

BACKGROUND OF THE INVENTION

In the clinical diagnosis of bacterial diseases, such as tuberculosis, a sample of sputum or other body fluid obtained from the patient is cultured to test for the presence of the particular bacterium of interest. Unfortunately, this is a relatively time-consuming process, generally requiring several days to produce a definitive result. During this time, a patient suspected of having tuberculosis, for example, must be isolated to prevent further spread of the disease.

The advent of DNA probes, which can identify a specific bacteria by testing for the presence of a unique bacterial DNA sequence in the sample obtained from the patient, has greatly increased the speed and reliability of clinical diagnostic testing. A test for the tuberculosis mycobacterium, for example, can be completed within a matter of hours using DNA probe technology. This allows treatment to begin more quickly and avoids the need for long patient isolation times.

In the use of DNA probes for clinical diagnostic purposes, a nucleic acid amplification reaction is usually carried out in order to multiply the target nucleic acid into many copies or amplicons. Examples of nucleic acid amplification reactions include strand displacement amplification (SDA) and polymerase chain reaction (PCR). Detection of the nucleic acid amplicons can be carried out in several ways, all involving hybridization (binding) between the target DNA and specific probes.

Many common DNA probe detection methods involve the use of fluorescein dyes. One known detection method is fluorescence energy transfer. In this method, a detector probe is labeled both with a fluorescein dye that emits light when excited by an outside source, and with a quencher which suppresses the emission of light from the fluorescein dye in its native state. When DNA amplicons are present, the fluorescein-labeled probe binds to the amplicons, is extended, and allows fluorescence emission to occur. The increase of fluorescence is taken as an indication that the disease-causing bacterium is present in the patient sample.

Several types of optical readers or scanners exist which are capable of exciting fluid samples with light, and then detecting any light that is generated by the fluid samples in response to the excitation. For example, an X-Y plate scanning apparatus, such as the CytoFluor Series 4000 made by PerSeptive Biosystems, is capable of scanning a plurality of fluid samples stored in an array or plate of microwells. The apparatus includes a scanning head for emitting light toward a particular sample, and for detecting light generated from that sample. The apparatus includes first and second optical cables each having first and second ends. The first ends of the optical cables are integrated to form a single Y-shaped "bifurcated" cable. The scanning head includes this end of the bifurcated optical cable. The second end of the first optical cable of the bifurcated cable is configured to receive light from a light emitting device, such as a lamp, and the second end of the second cable of the bifurcated cable is configured to transmit light to a detector, such as a photomultiplier tube.

During operation, the optical head is positioned so that the integrated end of the bifurcated optical fiber is at a suitable position with respect to one of the microwells. The light emitting device is activated to transmit light through the first optical cable of the bifurcated optical cable such that the light is emitted out of the integrated end of the bifurcated optical cable toward the sample well. If fluid sample fluoresces in response to the emitted light, the light produced by the fluorescence is received by the integrated end of the optical fiber and is transmitted through the second optical fiber to the optical detector. The detected light is converted by the optical detector into an electrical signal, the magnitude of which is indicative of the intensity of the detected light. This electrical signal is processed by a computer to determine whether the target DNA is present or absent in the fluid sample based on the magnitude of the electrical signal.

In this type of X-Y plate reader apparatus, the reader head must be repositioned for each well. Accordingly, if the microwell array is a standard microwell array having 12 columns of 8 microwells (96 microwells total), the reader head must move 96 times for the entire microwell array to be read. This excessive movement increases the amount of wear and tear experienced by the apparatus. Furthermore, the control system for controlling the positioning of the head reader must be sophisticated enough to ensure that the integrated end of the optical fiber in the reader head is positioned correctly for each microwell so that the readings are taken at identical locations (e.g., the center) of each microwell. If the integrated end of the optical fiber is not aligned correctly with the microwell, the fluid in the microwell may not receive an adequate amount of excitation light and may therefore not fluoresce properly. Furthermore, any fluorescence that does occur may not be completely detected, because that light may not transmit properly into the integrated end of the bifurcated optical fiber. Accordingly, unless the positioning of the head reader is maintained precise for each individual well, erroneous readings may occur.

Another existing type of apparatus is described in U.S. Pat. No. 5,473,437, to Blumenfeld et al. This apparatus includes a tray having openings for receiving bottles of fluid samples. The tray includes a plurality of optical fibers which each have an end that terminates at a respective opening in the tray. The tray is connected to a wheel, and rotates in conjunction with the rotation of the wheel. The other ends of the optical fibers are disposed circumferentially in succession about the wheel, and a light emitting device is configured to emit light toward the wheel so that as the wheel rotates, the ends of the optical fibers sequentially receive the light being emitted by the light emitting device. That is, when the wheel rotates to a first position, a fiber extending from the wheel to one of the openings becomes aligned with the optical axis of the light emitting device and thus, the emitted light will enter that fiber and be transmitted to the opening. The apparatus further include a light detector having an optical axis aligned with the optical axis of the emitted light. Accordingly, if the sample in the bottle housed in the opening fluoresces due to the excitation light, the light emitted from the sample will transmit through the optical fiber and be detected by the detector. The wheel then continues to rotate to positions where the ends of the other optical fibers become aligned with the optical axis of the light emitter and light detector, and the light emission and detection process is repeated to sample the fluid samples in the bottles housed in the openings associated with those fibers.

As with the CytoFluor X-Y plate reader apparatus described previously, the apparatus described in U.S. Pat. No. 5,473,437 uses a single light emitter and a single light detector to test a plurality of fluid samples. However, instead of using a single bifurcated cable as in the X-Y plate reader apparatus, this apparatus uses a plurality of single optical cables which are individually dedicated to a particular sample. Nevertheless, like the X-Y plate reader apparatus, this apparatus requires mechanical movement between the fluorescent interrogation for each sample. That is, the apparatus is incapable of testing a plurality of samples with only one mechanical motion. Rather, the wheel must rotate to align the optical axis of the light emitter and light detector with each of the optical fibers associated with each of the respective samples. Because the control system used by the apparatus must assume that the appropriate optical fiber is aligned correctly for each sample, the chance of misalignment is significant. Furthermore, this constant movement imposes significant wear and tear on the apparatus.

Another type of optical testing apparatus is described in U.S. Pat. No. 5,518,923, to Berndt et al. That apparatus includes a plurality of light emitter/light detector devices for testing a plurality of fluid samples. The fluid samples are contained in jars which are placed in the openings of a disk-shaped tray. The plurality of light emitter/detector devices are disposed in the radial direction of the tray. Hence, as the tray rotates, the samples in each circular row will pass by their respective light emitter/detector device, which will transmit light into the sample and detect any light that is generated by the sample in response to the emitted light. In theory, this apparatus is capable of testing more than one sample at any given time. However, in order to achieve this multiple sample testing ability, the system must employ a plurality of light detectors and a plurality of light emitters. These additional components greatly increase the cost of the system. For example, photomultiplier tubes, which are generally quite expensive, are often used as light detector units in devices of this type. Hence, the cost of the unit is generally increased if more than one photomultiplier tube is used. However, it is desirable to use as few photomultiplier tubes as possible to maintain a competitive price for the apparatus. However, devices which employ a single detector (e.g., photomultiplier tube) are incapable of testing a plurality of samples without some type of mechanical motion for each test. Therefore, this multiple detection apparatus is somewhat impractical from a cost standpoint.

A detector apparatus is also described in U.S. Pat. No. 4,343,991, to Fujiwara et al. This apparatus employs a single light detector and a plurality of light emitting devices to read a sample on a sample carrier, which is a substantially transparent medium. In this apparatus, the plurality of light emitting devices transmit light through corresponding optical fibers. The light emitted by the optical fibers passes through the carrier and is received by corresponding optical fibers on the opposite side of the carrier. The receiving fibers terminate at a single light detector and the light emitters are operated to emit light at different times. Hence, light from only one of the emitters passes through the carrier at any given time and is detected by the detector, which outputs a signal proportional to the intensity of the detected light. Therefore, a single detector can be used to detect light from a plurality of light emitting devices. When the light passes through a portion of the carrier that includes a sample, the intensity of the light is decreased because some of the light is absorbed by the sample. The amount by which the light intensity is reduced is proportional to the concentration of the sample material in the sample. Because the signal output by the detector is proportional to the intensity of the detected light, the sample concentration can thus be determined based on the output signal.

Although the apparatus described in U.S. Pat. No. 4,343,991 eliminates the need for a mechanical movement for each sampling, the arrangement of the optical fibers on opposite sides of the carrier requires that the fibers be precisely aligned so that the light emitted by an optical fiber is detected properly by its corresponding optical fiber coupled to the light detector. The apparatus is therefore easily susceptible to erroneous readings if the light emitting optical fibers and light detecting optical fibers are not perfectly aligned. Furthermore, the light detecting fibers are not arranged to detect luminescence of the samples, but rather, the intensity of the light passing through the samples. In addition, since the light emitting fibers and light detecting fibers are on opposite sides of the carrier, enough space must be allocated in the apparatus to accommodate fibers on both sides of the area through which the carrier is conveyed, thus increasing the overall size of the apparatus.

Accordingly, a continuing need exists for an optical testing apparatus employing a single detector, such as a photomultiplier tube, which is capable of accurately performing a plurality of tests on a plurality of liquid samples without requiring a mechanical movement for each test.

SUMMARY OF THE INVENTION

An object of the present invention is to provide an apparatus which is capable of performing optical photoluminescence sampling samples, such as a DNA probe assay, on a plurality of fluid without requiring a mechanical movement for each sampling. A further object of the present invention is to provide an apparatus which is capable of detecting light emitted from a sample in response to excitation of the sample, such that a plurality of samples can be sampled without requiring a mechanical movement for each sampling.

Another object of the invention is to provide an apparatus that emits light toward a sample and detects light emitted from the sample through the same optical port, so that it is not necessary to align the light emitters and detectors on opposite sides of the sample.

A further object of the invention is to provide a sample scanning apparatus that has a heated sample housing stage which heats the samples while they are awaiting sampling and throughout the sampling process.

Another object of the invention is to provide a sample scanning apparatus that is capable of mapping the sample pattern prior to performing the sampling.

In order to achieve these objects, the present invention provides an optical scanning apparatus comprising a plurality of light emitting devices, such as light emitting diodes, which each emit light excitation through a respective optical fiber toward a respective fluid sample in a plurality of fluid samples in a time-staggered manner. Therefore, fluorescence is generated in each of the fluid samples in response to the excitation light at different times corresponding to the times at which the light is transmitted to the samples. Hence, a single detector can detect the light emitted from a plurality of samples because the light is emitted from each sample at a different time. The apparatus further includes a plurality of bifurcated optical cables, from which excitation light can be emitted toward corresponding samples, and into which light emitted from the samples in response to the excitation light can be received and provided to a single detector.

The apparatus also includes a heated stage which houses the plurality of samples throughout the testing process. This heated stage, includes heating elements, and is made of a good thermal conductor, such as metal or the like, which conducts heat to the sample containers housed in the stage.

BRIEF DESCRIPTION OF THE DRAWINGS

These and other objects and advantages of the present invention will be more readily appreciated from the following detailed description taken in conjunction with the accompanying drawings, in which:

FIG. 7 is a rear perspective view of the stage assembly shown in FIG. 6A;

DETAILED DESCRIPTION OF THE PREFERRED EMBODIMENT

Figure 1:
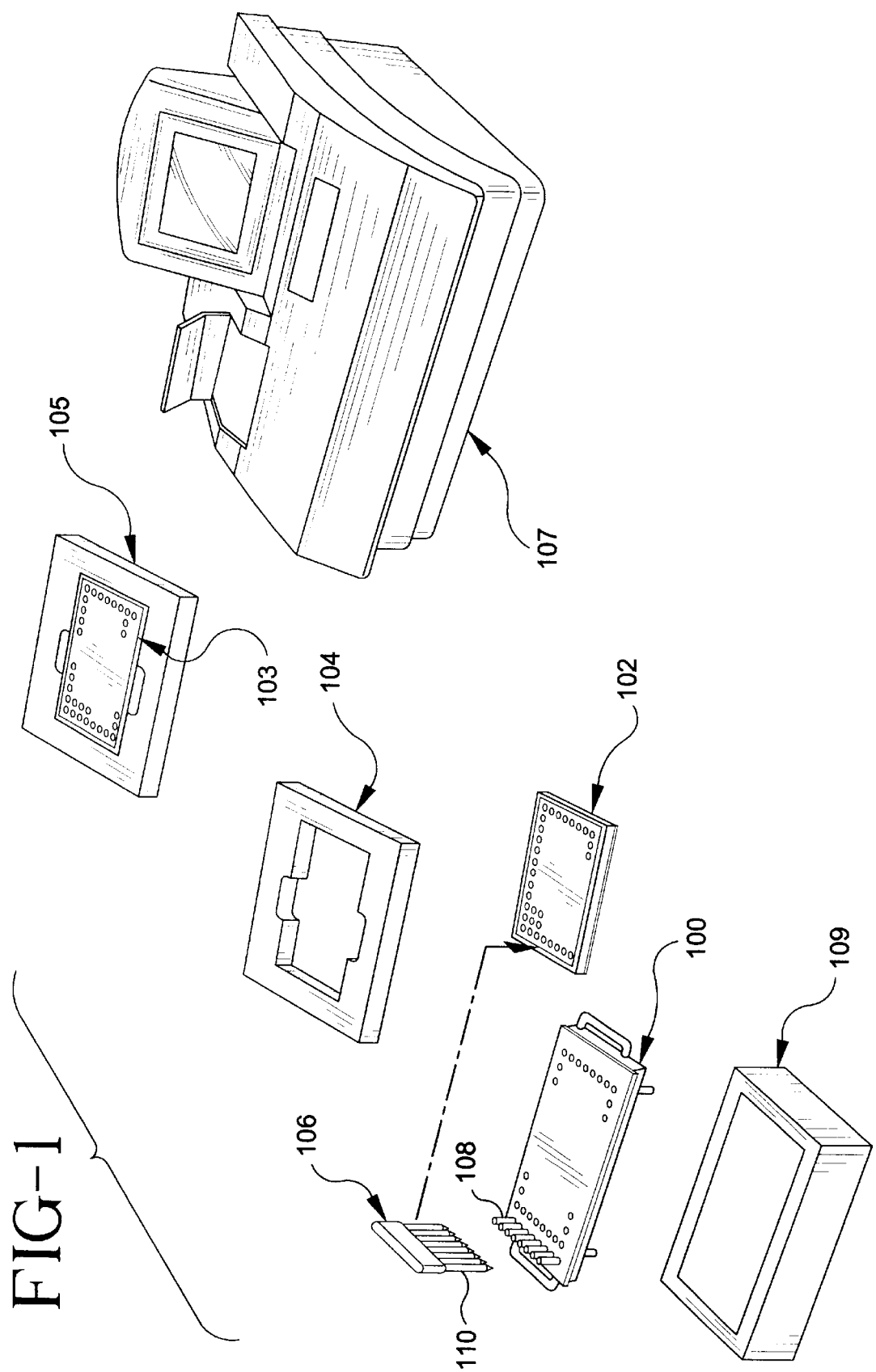
FIG. 1 illustrates an example of a testing system according to the present invention, which includes a sample tube rack, first and second microwell arrays, a microwell incubator and reader apparatus, and a pipetter for transferring the fluid samples stored in the sample tubes into the microwells of the first microwell array.
Figure 2:
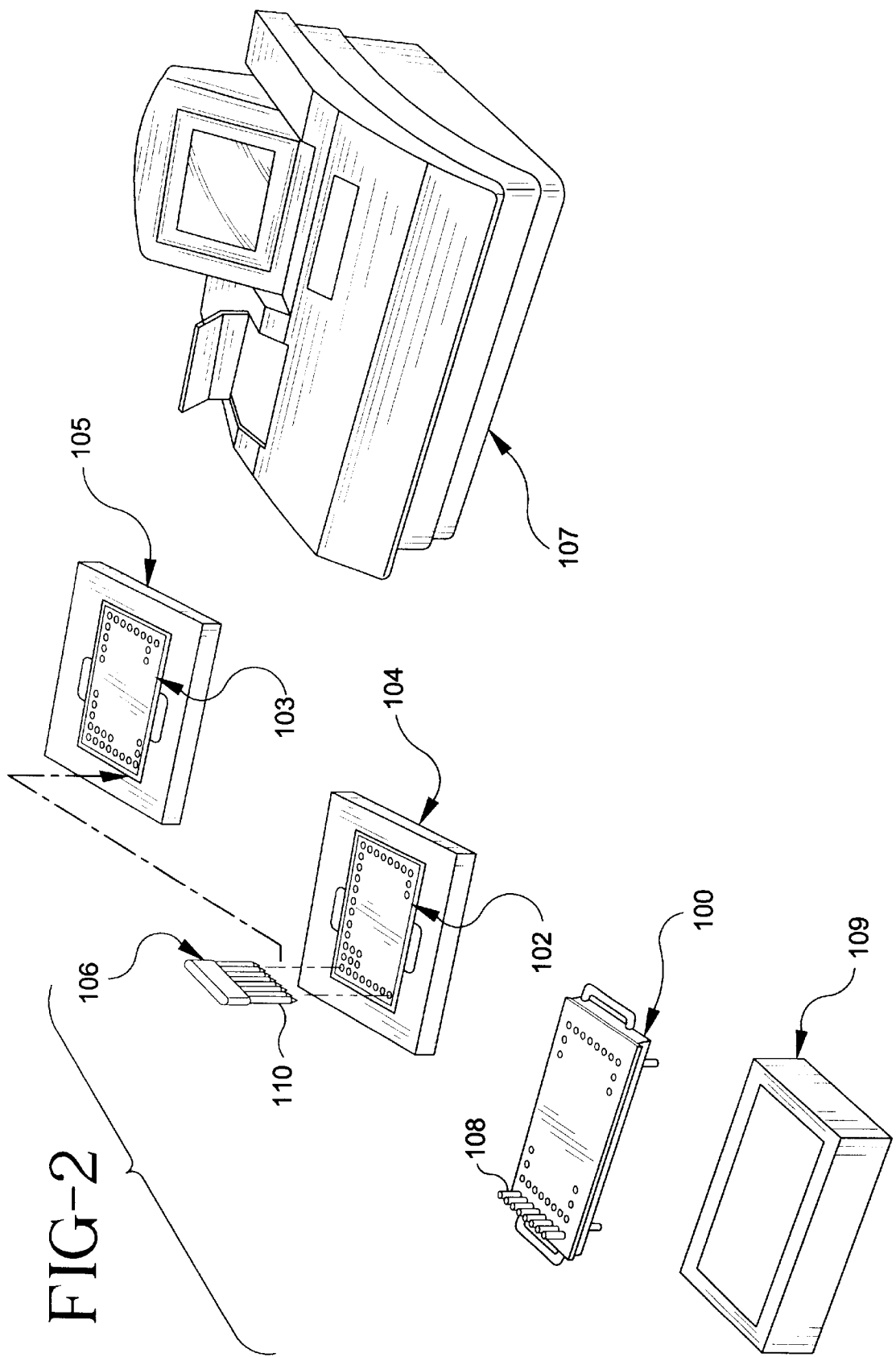
FIG. 2 illustrates the use of the pipetter in the system shown in FIG. 1 for transferring the fluid samples in the microwells of the first microwell array into the corresponding microwells of the second microwell array.
Figure 3:
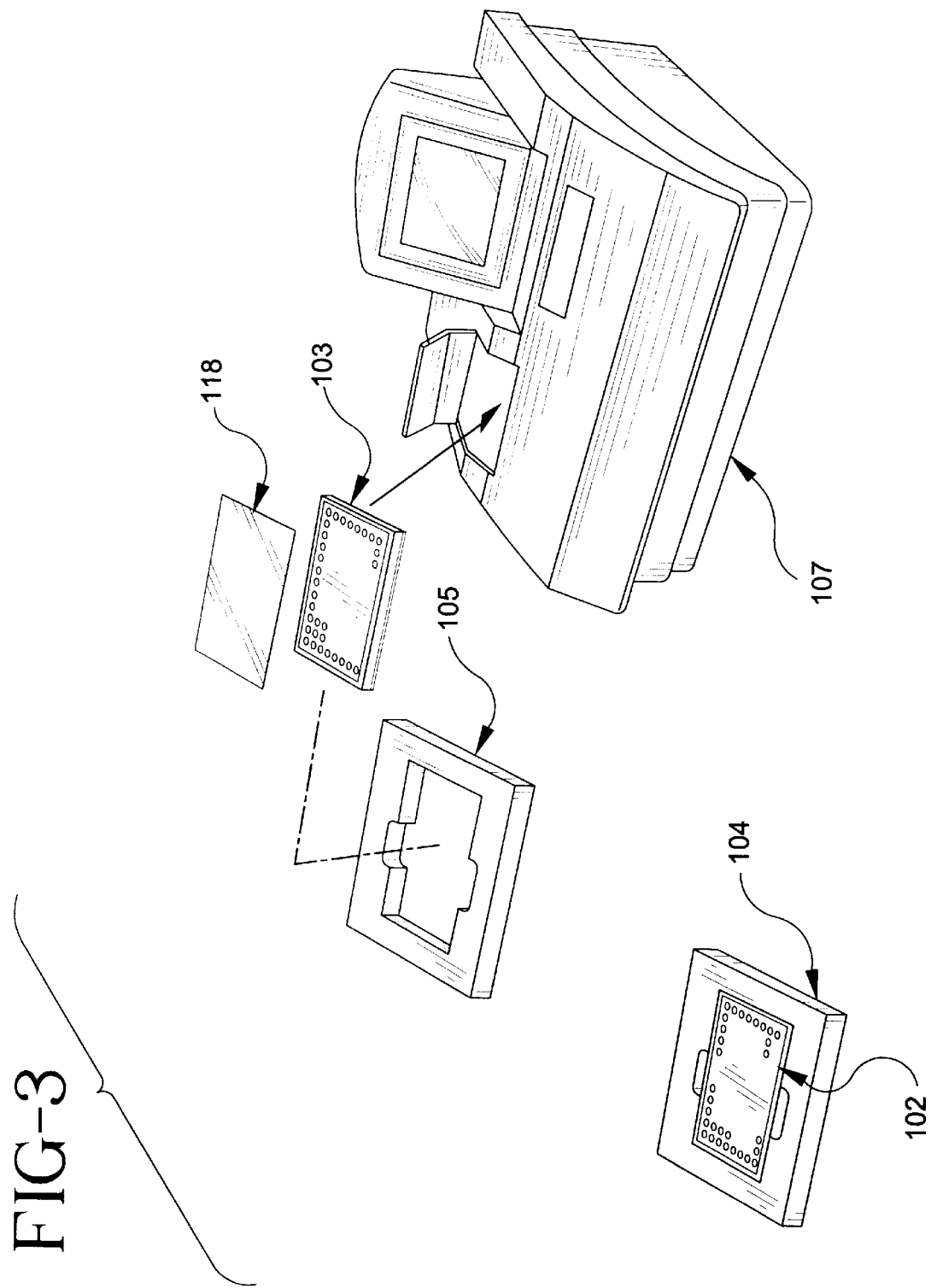
FIG. 3 illustrates the placement of the second microwell array into the microwell incubator and reader apparatus.

FIGS. 1–3 illustrate a system for performing DNA amplification and DNA probe detection which employs an automated microwell incubator and reader apparatus in accordance with a preferred embodiment of the present invention. Specifically, the system employs a sample tube rack 100, two microwell tray assemblies 102 and 103, a heating unit 104 and 105, a pipetting apparatus 106, and an automated incubator and reader apparatus 107.

Before the DNA amplification and testing is performed, a plurality of sample tubes 108 each containing an amount of sample fluid provided by a patient are placed in tube rack 100. The tube rack 100 includes 12 rows of 8 openings each and thus, can accommodate up to 96 sample tubes 108. Therefore, fluid samples from up to 96 different patients can be tested by this system during each run.

The tube rack 100 is placed in a lysing heater 109 which heats the fluid samples to a temperature that causes the cells in the fluid samples to burst open and release their DNA. After the tube rack 100 has been removed from the lysing heater 109, a pipetting apparatus 106 having 8 individual pipette tips 110 is used to draw the samples from an entire column of tubes 108. It is noted that the number of individual pipette tips 110 should always correspond to the number of tubes 108 in a column of the tube rack 100. As the pipette tips 110 are placed simultaneously into their respective tubes 108, some of the fluid sample in each respective vial is drawn into its respective pipette 110.

Figure 4:
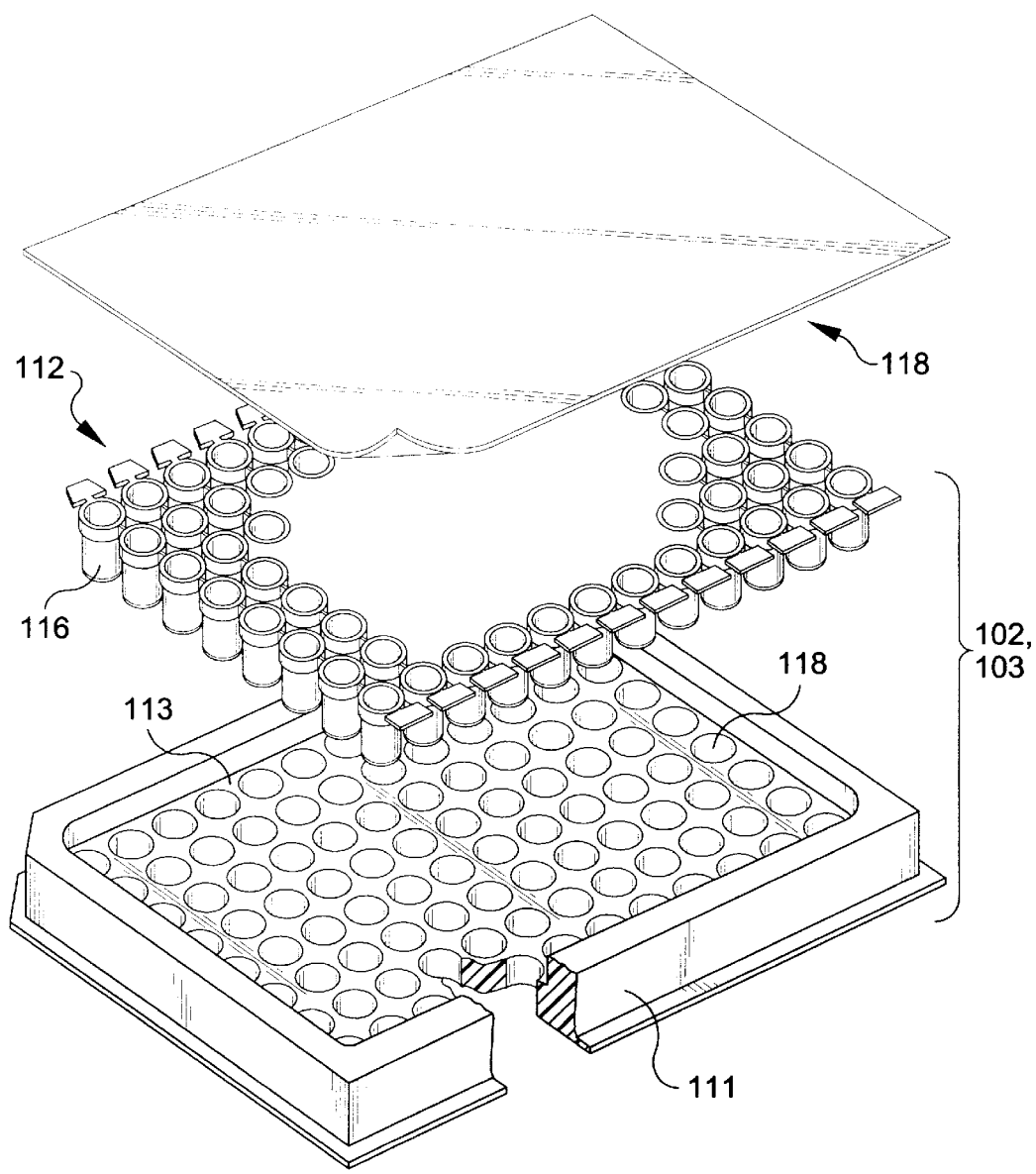
FIG. 4 is an exploded perspective view of a tray, a microwell array and a microwell array seal in accordance with an embodiment of the present invention.

The pipetting apparatus 106 is then conveyed by a lab technician, for example, toward the first tray assembly 102, which is known as the primer well tray assembly. As shown in more detail in FIG. 4, the tray assemblies 102 and 103 each include a tray 111 having a recess 113 into which a microwell array 112 is removably placed. The microwell array 112 can be a standard microwell array having 96 individual microwells 116 or a series of strips of 8 microwells, portions of a string of microwells, individual microwells, or any portion thereof.

However, a microwell array having any practical number of microwells can be used. The number of microwells can equal the number of openings in the tube rack 100, and the number of microwells 116 in each column should equal the number of tubes 108 in each column. However, this type of arrangement is not required, but can be any suitable arrangement.

When the microwell array 112 is placed in the recess 105, the individual microwells 116 are accommodated in a corresponding openings 118 in the tray 111. The 96 microwells of the standard microwell array are arranged in 12 columns of 8 microwells each. Accordingly, the tray 103 includes 12 columns of 8 openings 118 to accommodate the 8×12 array of microwells. As shown, the openings 118 pass entirely through the tray 111. The tray 111 is preferably made of metal, such as aluminum, which is a good heat conductor. The tray 111 could also be made of plastic or any other suitable material. The configuration of the tray 111 enables it to heat the microwells about their circumference or leaving the bottoms of the microwells unobstructed for optical excitation and detection as will be described in detail shortly.

When the pipetting apparatus 106 is conveyed to the tray assembly 102, the individual pippette tips 110 are aligned with a column of microwells 116, so that each individual pipette 110 will be above a corresponding one of the microwells 116. A lab technician then manipulates the pipetting apparatus 106 to cause the individual pippette tips 110 to release at least a portion of the fluid sample stored therein into their corresponding microwells. Hence, the 8 individual pippette tips 110 will fill the 8 individual microwells 116 in one column of microwells.

The individual pippette tips 110 are then released from the pipetting apparatus 106, and a fresh set of 8 individual pippette tips 110 are attached to the pipetting apparatus 106. The above process is then repeated for the next column of tubes 108. That is, the 8 new individual pippette tips 110 are aligned with the second column of tubes 108, and the pipetting apparatus 106 is manipulated so that a portion of the fluid sample in each of the tubes 108 in the second column are drawn into corresponding individual pippette tips 110. The pipetting apparatus 106 is then conveyed over to the tray assembly 102 so that the individual pippette tips 110 align with the second column of microwells 116 in the microwell array 112. At least a portion of the fluid sample stored in each of the individual pippette tips 110 is released into its corresponding microwell 116. These used pipette tips 100 are then released from the pipetting apparatus 106 and replaced with a fresh set of pippette tips 110, and the process is repeated until fluid samples from all of the 96 sample tubes 108 are conveyed to the corresponding 96 microwells 116.

The microwells 112 that have been filled with fluid samples can then be temporarily covered with a cover or the like and the fluid samples allowed to incubate at either room temperature or a certain desired temperature for a period of time. Each of the microwells 112 includes primers and fluorescence energy detection reagents (probes) in dried form on its interior surface.

Alternatively, instead of conveying the 96 samples into 96 microwells, if desired, the samples in the 8 tubes 108 can be released onto more than 1 microwell each. For example, the system can use 3 microwells for each sample. In this event, the sample from each tube 108 is deposited by its respective pipette tip 110 into 3 microwells. Hence, a maximum of 32 tubes will be present in the tray 100 to provide samples to the 96 microwells of the 3 wells for each sample, with 1 well containing 1 type of reagent to identify a particular disease, another well containing another type of reagent to identify another disease, and the third well can be used as an internal amplification well that includes a reagent which will cause the well to give a positive test result at all times (even if the patient does not have the particular disease) for control purposes.

The tray assembly 102 including the microwell array 112 is then placed in the heating unit 104 for further incubation. After a predetermined heating period at about 70° C., the pipetting apparatus 106 is used to convey the fluid samples in the 96 microwells of the microwell array 112 into the 96 microwells of the second microwell array 112 in a second tray assembly 102, which is known as the amplification well assembly. It is noted that while the fluid samples are incubating in the first microwell array 112 at room temperature and in the heating unit 104, the second tray 103 containing the second microwell array 112 is being preheated in its corresponding heating unit 104. Hence, after the appropriate amount of heating time has elapsed, the pipetting apparatus 106 uses the individual pippette tips 110 to convey the fluid samples from the first microwell array 112 to the second microwell array 112 on a column by column basis. The 8 individual pippette tips 110 of the pipetting apparatus 106 are aligned with the first column of microwells 116 in the first microwell array 112, and the pipetting apparatus 106 is manipulated so that the fluid samples in those microwells are drawn into the corresponding individual pippette tips 110. The pipetting apparatus 106 is then conveyed to the second tray assembly 103 so that the individual pippette tips 110 align with a column of individual microwells 116. The pipetting apparatus 106 is then manipulated to discharge the fluid samples in the individual pippette tips 110 into their corresponding microwells in the second microwell array 112. The used individual pippette tips 110 are released and replaced with a new set of individual pippette tips 110 and the process is repeated for the next column of microwells.

The process is continued until all of the 96 fluid samples stored in the 96 microwells 116 in the first microwell array 112 have been transferred into the corresponding microwells 116 in the second microwell array 112. A seal 118, which can be a transparent plastic sheet, an opaque or translucent cover, or any suitable type of cover made out of any suitable material, is placed over the top of the microwells 116 on the microwell array 112, and the tray assembly 103 containing the second microwell array 112 is further heated in the heater 104 so that the 96 fluid samples in the microwells 116 will incubate. The seal 118 has an adhesive on one of its surfaces, which enables the seal to adhere to the top of the microwell array 112. The seal 118 acts to form a tight seal for each of the microwells, to prevent foreign substances from entering the microwells, and also prevents cross-contamination between different microwells in the array and prevents amplified materials from exiting the microwells. The microwells 116 contain enzymes, also in dried form, which allow the DNA amplification and detection reactions to proceed.

After the preparation process described above has been performed, the entire second tray assembly 103 containing the sealed microwell array 112 in which the 96 fluid samples are stored is conveyed into the automated incubator and reader apparatus 107. The microwells are then repeatedly incubated and optically scanned while the tray is incubating to determine which of the fluid samples contains the target DNA sequence.

Figure 5:
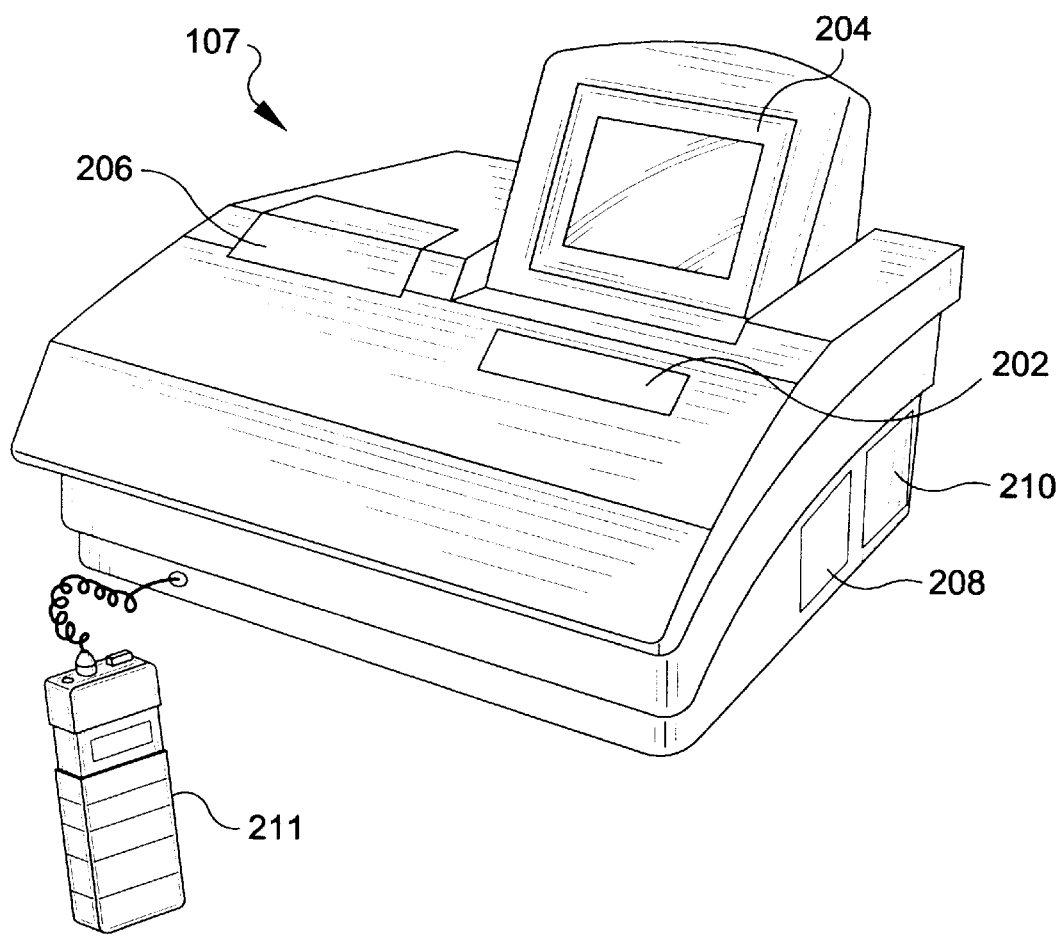
FIG. 5 is a front perspective view of the microwell incubator and reader apparatus in the system shown in FIG. 1.

FIG. 5 is a perspective view of an example of the automated incubator and reader apparatus 107 according to an embodiment of the present invention. The apparatus 107 includes a keypad 202, including soft keys or the like, which enables an operator to enter data and control the operation of the apparatus 107. The apparatus further includes a display screen 204, such as an LED display screen or the like, for displaying information in response to the operator's commands entered via the keypad 202, and for displaying data pertaining to the scanning information gathered from the samples in the manner described below. The apparatus also includes a door 206 through which the tray assembly 103 containing the microwell array 112 is inserted into the apparatus 107.

As illustrated, the apparatus includes a stage assembly 208 which houses the tray assembly 103 and conveys the tray assembly 103 during the scanning operation described below. The apparatus 107 further includes a control unit 210 which, as described below, includes a microcomputer and other scanning control equipment and processing equipment which controls the overall operation of the apparatus 107. The apparatus 107 can further include a bar code scanner 211 which can be used to read, for example, bar code information present on patient identification labels on the tubes 108.

Figure 6A:
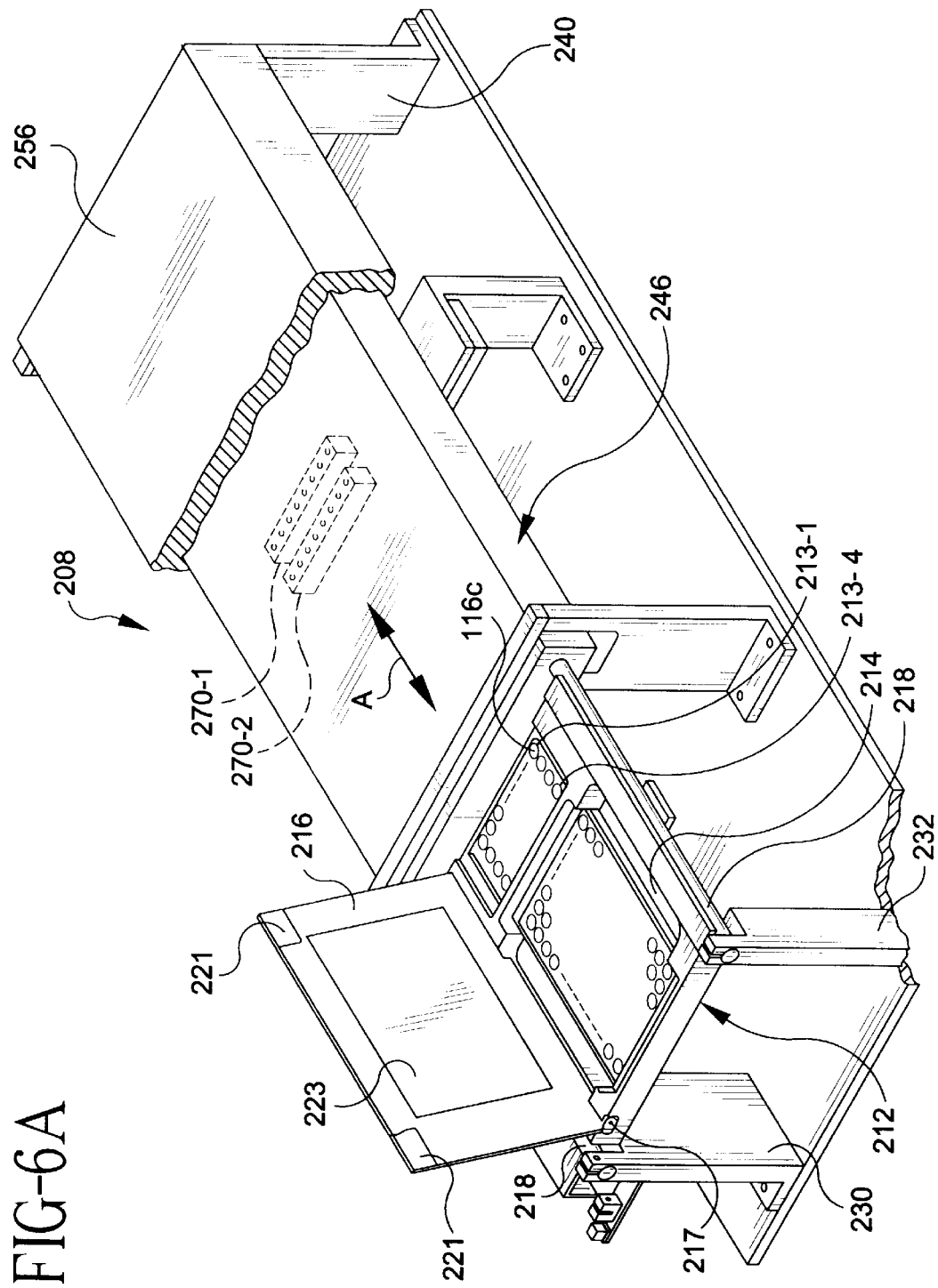
FIG. 6A is a front perspective view of an example of a stage assembly employed in the apparatus shown in FIG. 5, for receiving and conveying a tray assembly shown in FIG. 4.

FIG. 6A is a front perspective view of the stage assembly 208 of the apparatus 107 shown in FIG. 5. The stage assembly 208 includes a stage 212 having a tray accommodating portion 214 into which is placed the tray assembly 103. In one embodiment, the tray accommodating portion 214 is a hole open through the bottom of the stage 212. Therefore, the bottoms of the 96 transparent microwells 116 of the microwell array 112 housed in the tray 103 can be viewed from underneath the stage 212. The stage further includes a lid 216 which is pivotably connected to the stage 212 by a hinge 217.

It is noted that the stage 212 is preferable made of a material having good thermal conductivity, such as metal (e.g., aluminum), but can be made of any suitable material. The tray includes a heating element 219 which is used to conduct heat to the tray assembly 112.

Figure 6B:
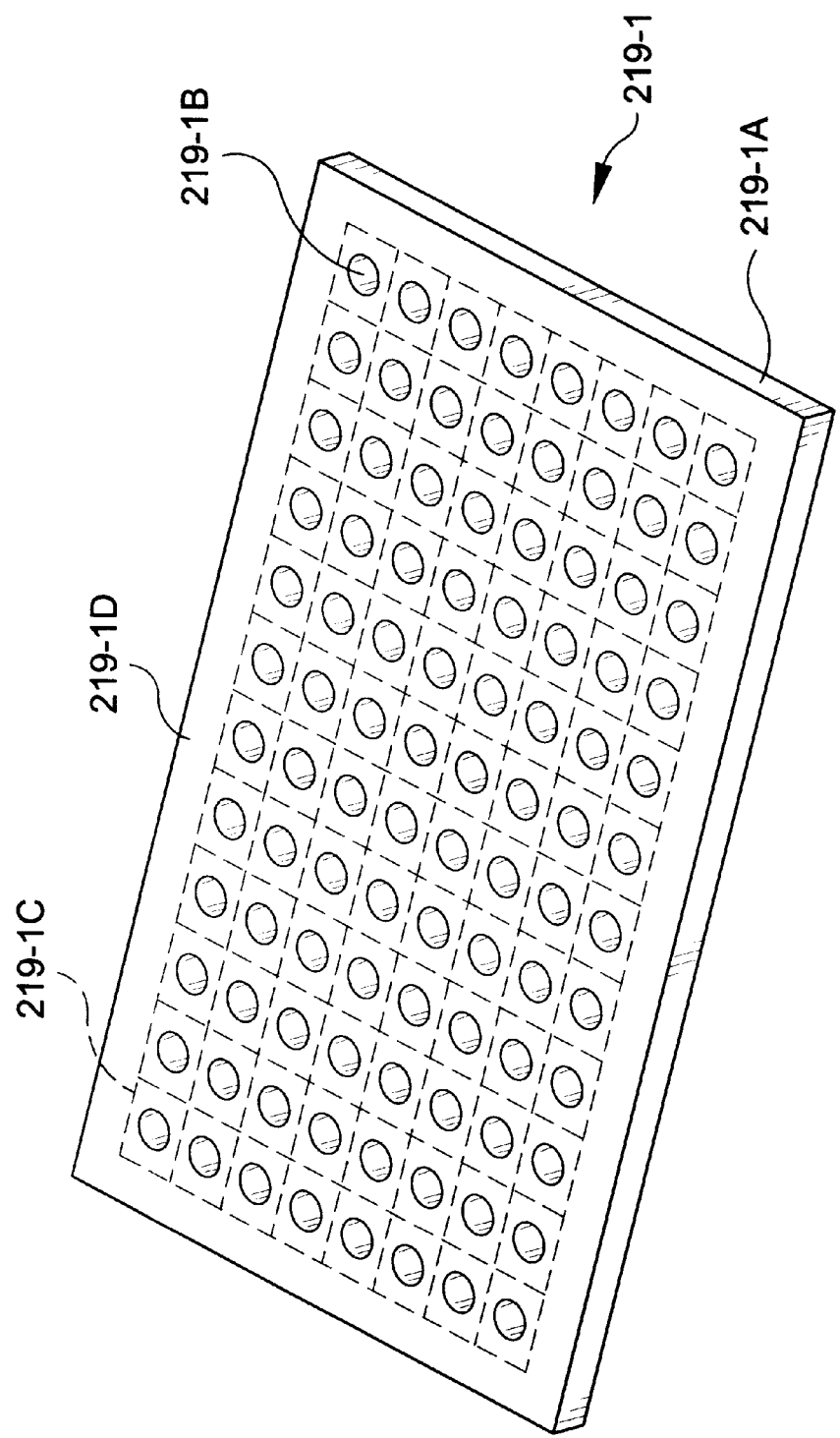
FIG. 6B is an example of a heating element of the stage of the stage assembly shown in FIG. 6A.

The heating element 219 can be a resistive element-type heating element, which radiates heat when an electrical current is passed through the resistive element. The resistive element can be bonded by an adhesive to the stage 212, for example, about the periphery of the stage. Alternatively, as shown in FIG. 6B, the heating element 219 can be a heated mask 219-1 that is disposed in the plate accommodating portion 214. The heated mask 219-1 is constituted by a metal plate-like portion 219-1A having 96 openings 219-1B which correspond to the 96 microwells in the microwell array 112. The heated mask 219-1 can be integral with the stage 212, or removably or permanently attached to the stage 212. The heated mask 219-1 is positioned in the plate accommodating portion 214 so that each of the 96 wells of the well array 112 will align with a respective one of the 96 openings in the heated mask 219-1 when the plate 104 is placed in the plate receiving portion 214.

The heated mask 219-1 is further constituted by a pattern of resistive elements, such as a resistive element trace 219-1C that is either embedded or etched directly on the metal plate-like portion, or is attached to the metal plate-like portion by a bonding material 219-1D, such as a plastic, composite or the like which can withstand high temperatures. The resistive element trace surrounds each of the openings, as illustrated, to act as a localized heating element for each opening and hence, each well 116 in the microwell array 112. Accordingly this heated mask 219-1 will function to further provide conductive heating to the block 103 and thus, to each microwell 116.

The heated stage 212 having either type of heating element 219 or 219-1 described above, keeps the tray assembly 103 heated at all times (e.g., when the stage 212 is outside of the oven described below). Furthermore, the heated stage 212 brings the samples in the microwells 116 of the microwell array 112 in the tray assembly 103 back up to the desired incubation temperature (approximately 52.5° C.) after the tray assembly 103 has been transferred to the tray receiving portion 214 of the stage from the heating block 105.

Alternatively, the heated stage 212 can function as the second heating block 105 to pre-heat the tray assembly 103. In this event, when the fluid samples are transferred from the primer microwells 116 in the primer microwells 116 in the amplification tray assembly 103, the tray assembly 103 need not be transferred into the stage 212 because it is already present in the stage 212. Accordingly, the heating block 105 can be eliminated. This provides better thermal control over the samples in the microwells tray assembly 103.

As further shown in FIG. 6A, the lid 216 of the stage 212 can include magnetic devices 221, such as magnets, which will be attracted to the stage 212 when the lid 216 is closed to urge the lid 216 toward the stage 212. If the stage 212 is made of material which does not attract the magnets 221, the stage 212 can include metal, brass or the like which are aligned with he magnets 221 when the lid 216 is in the closed position and thus attracts the magnets 221.

Alternatively, the magnets 221 can be positioned on the stage 212, and the lid 216 itself can be made of a material, such as metal or the like, which attracts the magnets 221. Also, magnets of opposite poles can be on the lid 216 and stage 212 to increase the attraction when the lid 216 is closed.

The lid 216 can further include a conformal coating 223, such as foam rubber or the like, or the surface of the lid 216 that opposes the microwell array 112 when the lid 216 is closed. this conformal coating coating 223 helps to hold the tray assembly in position in the tray receiving portion 214, and also ensures that the lid 216 provides even or substantially even pressure against the cover 118, to further cause the cover 118 to create a tight seal around the openings of each of the microwells 116. These tight seals further prevent the fluid samples from leaking or splashing out of their respective microwells.

When the carriage is positioned in its load position approximately as shown in FIG. 6A, the lid 216 aligns with or substantially aligns with lid door 206 of the apparatus 107. Hence, an operator can access the tray accommodating portion 214 of the stage 212 by opening the door 206 of the apparatus 107 and the lid 216 of the stage 212. After the tray assembly 103 has been inserted in the heating block accommodating portion 214, the lid 216 is closed to secure the tray assembly 103 in the heat accommodating portion 214, and to act as a further cover for the microwells 116.

Additionally, as described in more detail below, the stage 212 includes a plurality of one to four columns 215-1 through 215-4 (e.g. four in this embodiment) of calibration microwells 116C. The calibration microwells 116C each include a calibration marker, which can be a solid phase dye which fluoresces when excited with light having a particular wavelength. As discussed in more detail below, the calibration wells 116C are used to map the positions of all of the microwells 116 of the tray assembly 103 housed in the stage 212, and further, are used to calibrate the voltage of the photomultiplier tube (discussed later) which functions as a light detecting device for sensing light emitted by the markers.

As illustrated in FIG. 6A and further in FIG. 7, the stage is slidably coupled to rails 218 and thus, can be conveyed back and forth in directions along arrow A. As shown specifically in FIG. 7, the stage includes a stepper motor 220 that is controlled by the microcontroller in the control unit 210 (FIG. 5) to convey the stage 212 in the manner described below. Specifically, the stepper motor 220 has a pulley 222 which drives a belt 224 that passes about pulley 222 and another pulley 226 at the end of the stage assembly 208 opposite that at which the stepper motor 220 is disposed. The belt 224 is coupled to the stage 212 by, for example, a bracket 228, so that as the belt 224 is driven, the stage will correspondingly be driven. As illustrated, the rails 218 along which the stage 212 is conveyed are supported by brackets 230, 232, 234, 236, 238 and 240 to be elevated above a platform 242 which function as the base of the stage assembly 208. The brackets 230–240 are mounted to the platform 242 by any suitable mounting devices, such as screws, rivets, bolts, or the like. The stepper motor 220 is also mounted to the platform plate 242 by a bracket 244, such that the pulley 222 is at a height equal or substantially equal to the height of pulley 226 from the platform 242, so that the driving motion of the stage is parallel or substantially parallel to the platform 242.

The stage assembly 208 further includes a heating oven 246 which includes heating units (not shown) to heat the interior of the oven 246 at a desired temperature which will further incubate the fluid samples stored in the microwells 116 of the tray assembly 103 housed in the stage 212. As the stage 212 is conveyed into the oven 246, the stage passes through a door 248 of the oven 246 which is pivotally coupled to the sidewalls 250 of the oven by pivot or hinge 252. Hence, as the stage 212 passes completely through the door 248, the door will swing shut to keep the heat generated in the oven 246 inside the oven 246. As further shown, a layer of insulation 254 encloses the oven 246 to further keep the heat generated in the oven 246 from radiating out of the oven 246. The insulation 254 can be any suitable type of insulation, such as foam rubber or the like.

As shown in FIG. 7 specifically, the bracket 228 includes a plurality of flags 258 which are used to monitor the position of the stage 212 along the rails 218. To do this, the stage assembly 208 includes a plurality of sensors 260-1 through 260-5 which detect the presence of the flags 258 as the stage 212 is conveyed, and provide signals indicating the presence of the flags 258 to the microcontroller.

Figure 8:
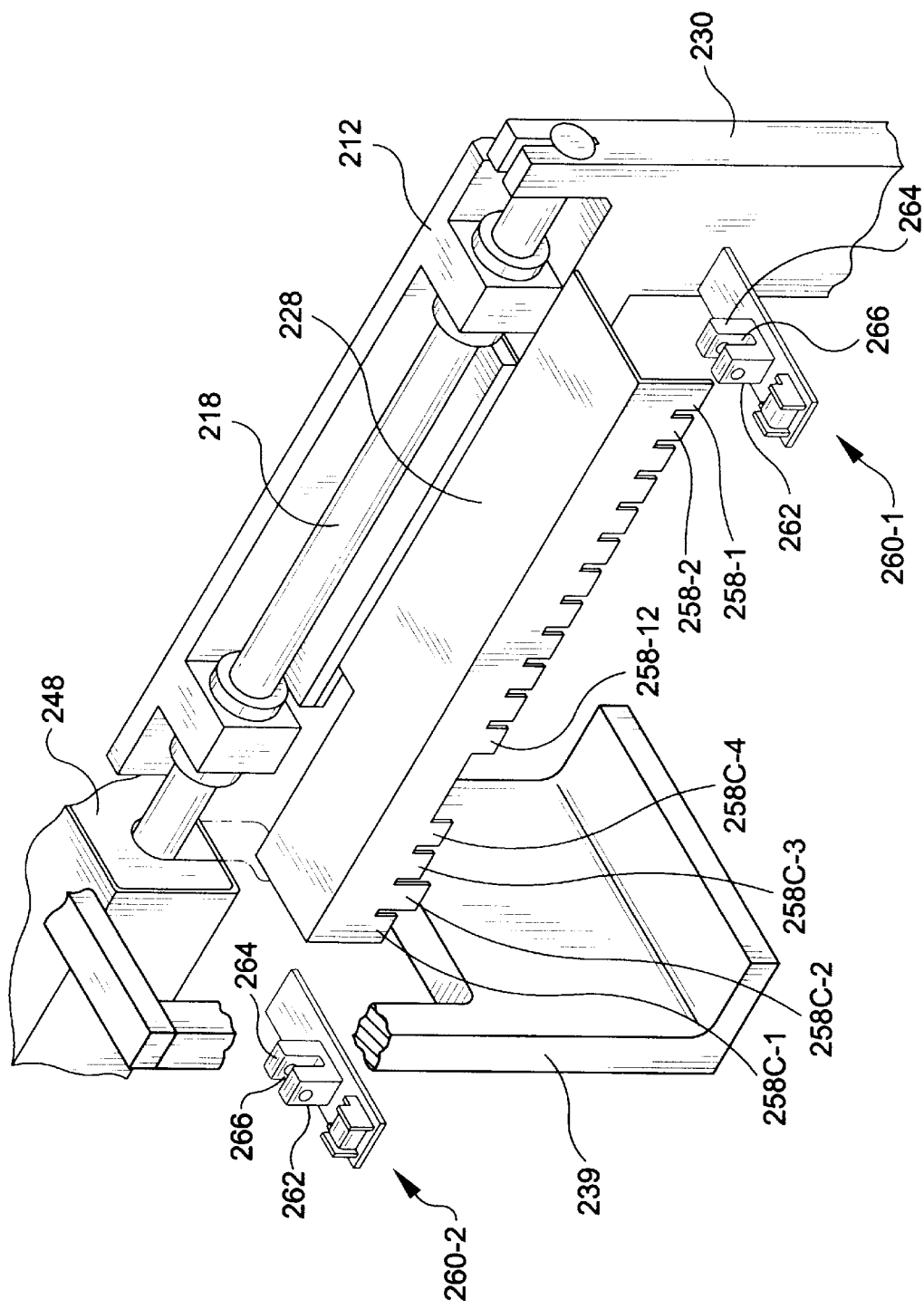
FIG. 8 is a detailed view of a portion of the stage assembly, as shown in FIG. 7.

As illustrated in more detail in FIG. 8, the sensors 260-1 through 260-5 each are an optical sensor including a light emitting device 262, such as a LED or the like, and a light detecting device 264, such as a photodiode, phototransistor, or the like. The light emitting device 262 emits light in the direction of the light detecting device 264, which is detected by detecting device 264 as long as no object passes through opening 266 between the light emitting device 262 and light detecting device 264. However, as the stage 212 is conveyed back and forth in the direction along arrow A, the flags 258 will pass one by one between the middle three sensors 260-2, 260-3 and 260-4. Also, when the stage 212 is at the loading position (approximately shown in FIGS. 7 and 8), the leftmost flag 258-12 will be positioned between light emitting device 262 and light detecting device 264 of sensor 260-1. Also, when the stage 212 is positioned at the "home" position, which is the rightmost position along the rails 218, the second calibrator well (described later) flag 258C-2 is positioned between the light emitting device 262 and light detecting device 264 of the sensor 260-5.

As illustrated, when a flag 258 passes into opening 266 in any sensor 260-1 through 260-5 (e.g., sensor 260-2), the flag 258 will block the light being emitted by light emitting device 262 from being detected by light detecting device 264. As is described in more detail below, the light detecting device 264 of that sensor will provide a corresponding signal to the microcontroller in the control box 210 indicating the presence of a tooth at the particular sensor. The microcontroller will process the information as appropriate to control the stepper motor 222 to move the stage in the proper manner.

Figure 9:
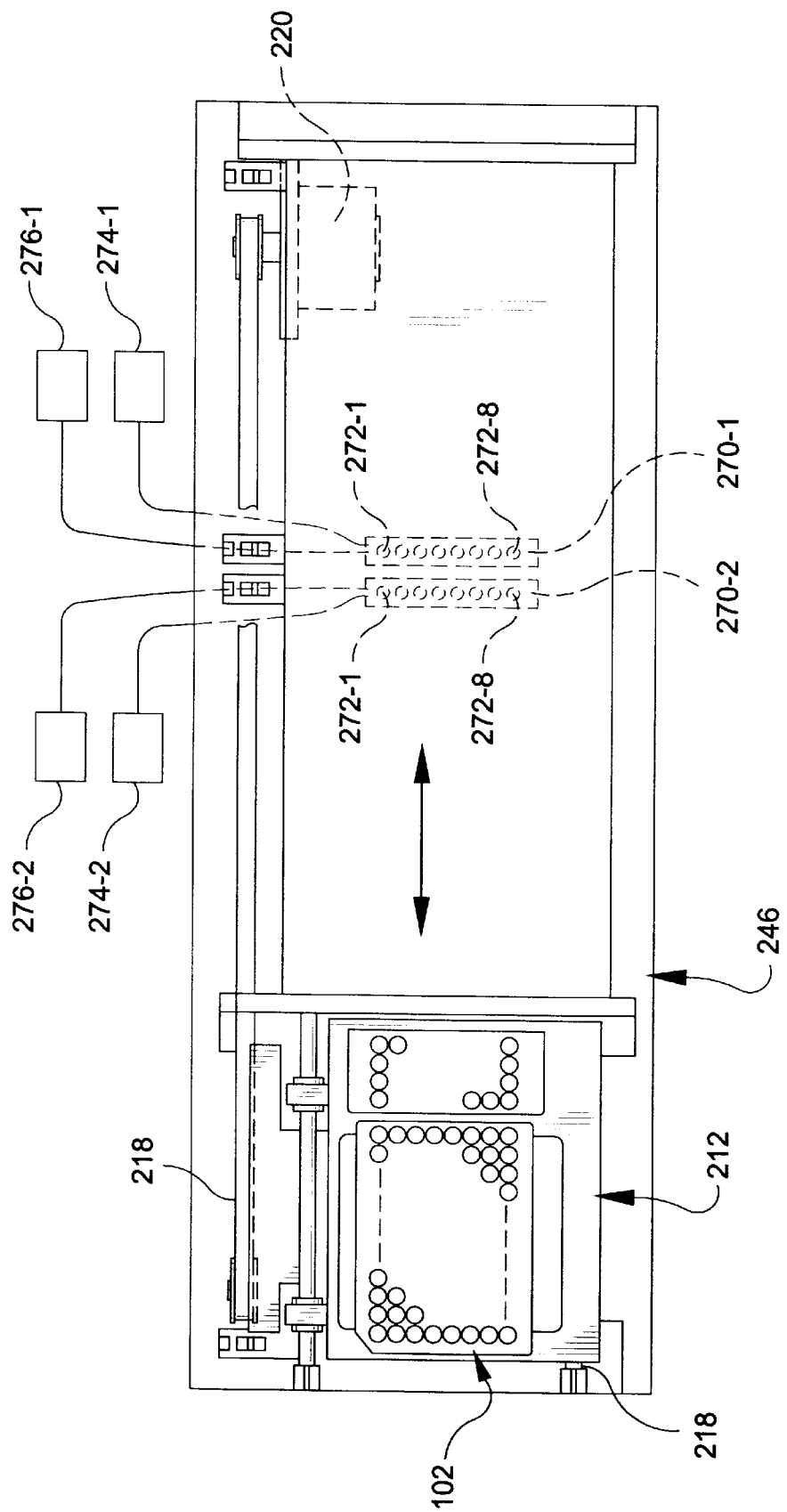
FIG. 9 is a top plan view of the stage assembly shown in FIGS. 6A and 7.

FIG. 9 illustrates a top plan view of the stage assembly 208 in which portions of the insulating material 256 and oven wall 246 have been cut away to expose the light sensing bars 270-1 and 270-2 which are used to sense the presence of fluorescence in the microwells 116 housed in the stage 212. As illustrated, as the stage 212 is conveyed back and forth along direction A, the columns of microwells 216 will pass over sensor bars 270-1 and 270-2. Sensor bars 270-1 and 270-2 each include a plurality of light emitting/ detecting ports 272, the number of which corresponds to the number of microwells 112 in a column in the microwell array 112. In this embodiment, each scanning bar 270-1 and 270-2 includes 8 light emitting/detecting ports 272 which are spaced from each other at a distance corresponding to or substantially corresponding to the distance from which the microwells 116 in each column are spaced from each other. Hence, as illustrated, when a column of microwells 116 is directly over the light emitting/detecting ports 272, the 8 light emitting/detecting ports 272 will align with or substantially align with the centers of their corresponding microwells 116.

As further illustrated in FIG. 9, the light emitting/ detecting ports 272 of the first scanning bar 270-1 are coupled to a first array 274-1 of light emitting devices, such as LEDs or the like, and to a first detector 276-1, such as a photomultiplier tube or the like. Likewise, the light emitting/ detecting ports 272 of the second scanning bar 270-2 are coupled to a second array 274-2 of light emitting devices, such as LEDs or the like, and a second light detecting device 276-2, such as photomultiplier tube or the like.

Figure 10:
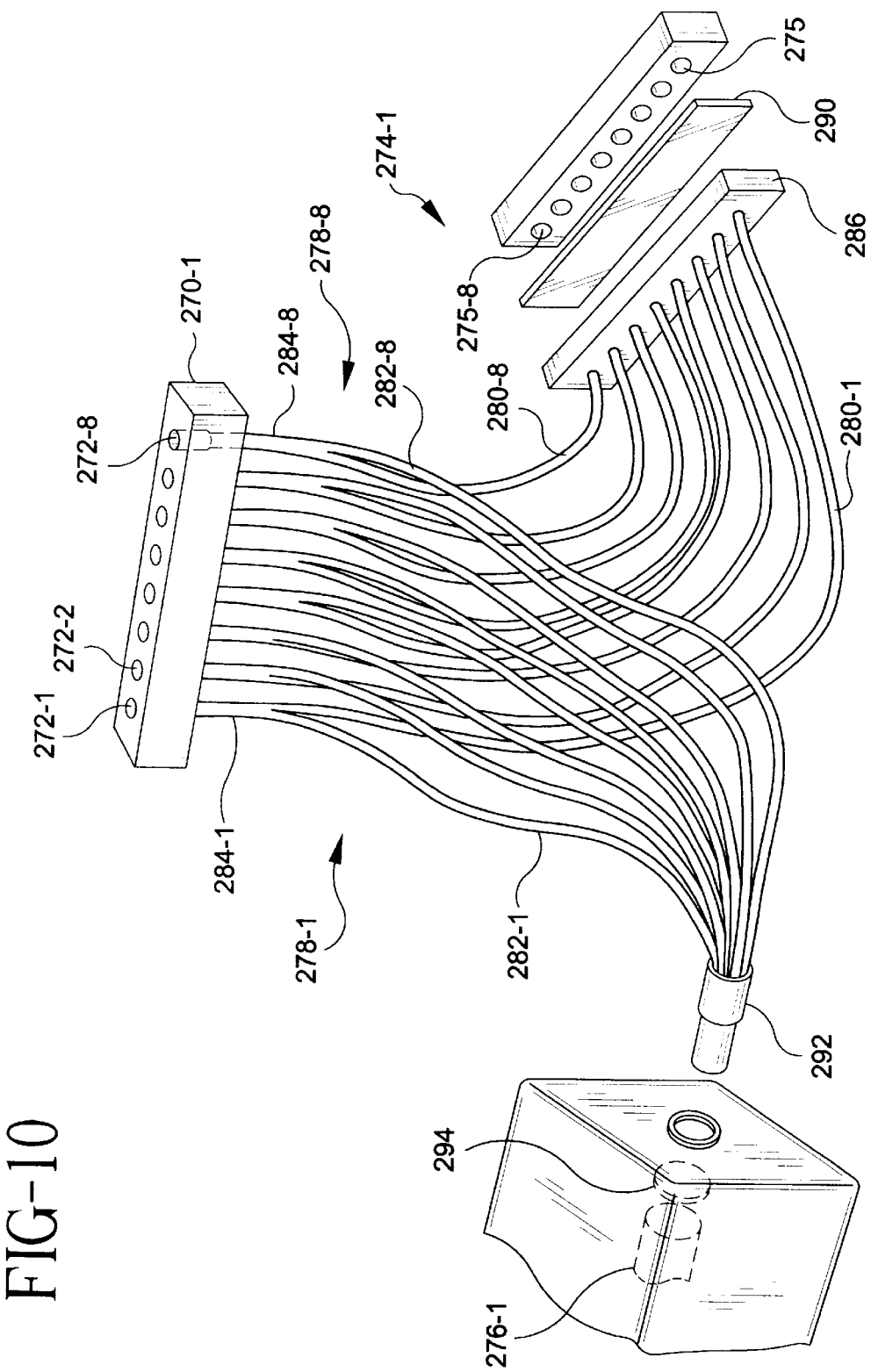
FIG. 10 is a diagram illustrating the layout of the fiber optic cables employed in the apparatus shown in FIG. 5.

FIG. 10 is a more detailed view of the connection between an exemplary one of the light bars 270-1 and its respective light emitting array 274-1 and light detector 276-1. Specifically, each light emitting/detecting port 272 is constituted by the integrated end of a bifurcated optical cable 278. In this embodiment, the scanning bar 270-1 includes 8 light emitting/detecting ports 272 and therefore, the arrangement includes 8 bifurcated cables 278.

Each bifurcated optical cable 278 includes two optical cables 280 and 282, each comprising a plurality of fiber optic strands. One end of the fiber optic cable 280 is integrated with one end of fiber optic cable 282, such that their individual optical fibers are integrated to form the integrated optical fiber end 284. As further shown, the other end of optical fiber 280 is inserted into an opening in a plate 286 of the light emitting array 274-1. Hence, cables 280-1 through 280-8 of the bifurcated fiber optic cables 278-1 through 278-8, respectively, are inserted in their respective holes in the plate 286, so that the ends of the optical fibers 280-1 through 280-8 are arranged sequentially in the openings of the plate 286.

The array 274-1 of light emitting devices further includes an array of LEDs 275-1 through 275-8, the number of which corresponding to the number of optical fibers 280-1 through 280-8 coupled to the plate 286. Accordingly, the 8 LEDs 275-1 through 275-8 are arranged to align with the respective ends of the optical fibers 280-1 through 280-8, respectively, inserted into the plate 286.

In this embodiment, the LEDs 275-1 through 275-8 emit light having a wavelength within the blue light spectrum (i.e., "blue" LEDs). To insure that the light entering the ends of each of the optical fibers 280-1 through 280-8 is essentially monochromatic, a blue filter 290 is positioned between the array of LEDs 275-1 through 275-8 and the plate 286 to filter out any undesired wavelengths in the blue light. Hence, the light being emitted from each LEDs 275-1 through 275-8 passes through the filter 290 before it enters its respective cable 280-1 through 280-8.

The other optical cables 282-1 through 282-8 of the 8 bifurcated fiber optic cables 278-1 through 278-8, respectively, each have ends which are integrated together in an "octopus" connector 292. That is, the individual strands of the optical cables 282-1 through 282-8 are integrated together to form an integrated cluster of fibers in the octopus connector 292. As shown, the octopus connector is positioned so that the integrated ends of the optical cables 282-1 through 282-8 face the light detector device 276-1. As stated above, the light detector device 276-1 is a photomultiplier tube or any similar type of light detecting device. To insure that the light entering the photomultiplier tube is essentially monochromatic, and, in particular, to insure that only the light produced by the fluorescence occurring within the microwells (and none of the blue light emitted by the LEDs) will enter the detector 276-1, a filter 294 is positioned between the connector 292 and the light detecting device 276-1. The filter 294 is a green filter which allows only light having a specific wavelength within the green light spectrum to pass.

As stated above, the operation of the stage and optical scanning equipment (e.g., the light emitting arrays, the light detectors, and so on) is controlled by the circuitry contained in control unit 210, which will now be described.

Figure 11:
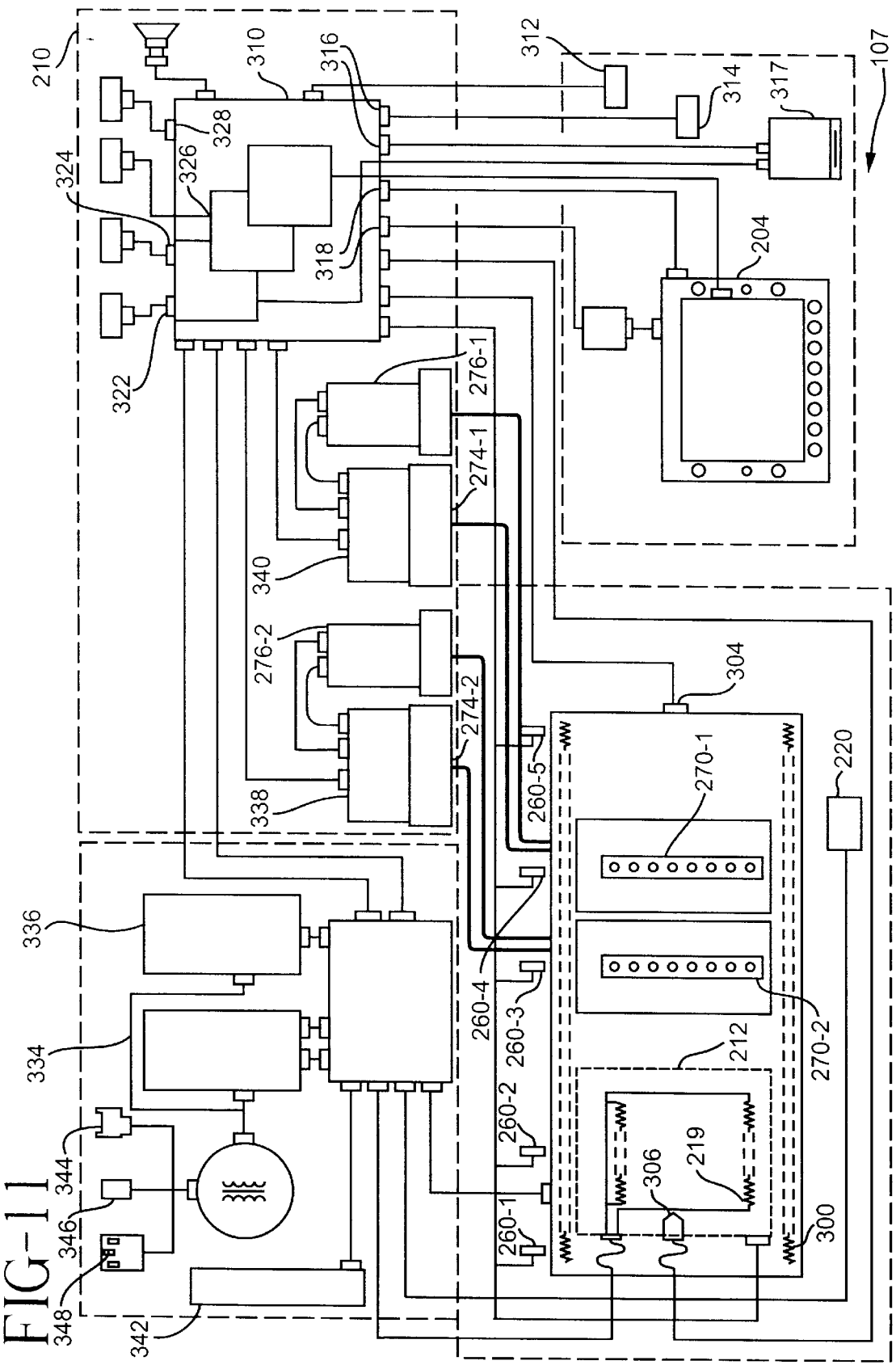
FIG. 11 is an electrical schematic diagram of the apparatus shown in FIG. 5.

FIG. 11 is a block diagram illustrating components of the apparatus 107, including the stage assembly 208 and control unit 210. As indicated, the stage assembly 208 includes the stage 212 into which the tray assembly 103 including the microwell array 112 is housed. The stage assembly 208 includes a plurality of heating elements 300 which are disposed inside the oven 246 to heat the ambient air inside the oven to a desired temperature. The stage 212 also includes heating elements 119 which conductively heat the tray assembly 103 in which the microwell array 112 is disposed and thus heat the fluid samples in the microwells 116-1. A heating sensor 304 and a heating sensor 306 provide signals to a microcontroller 310 which, in response, adjusts the heating elements 300 and 302 as appropriate to maintain the ambient heat in the oven 246 and the heating element 302 at the desired temperatures to keep the fluid samples at approximately 52.5° C.

In addition to controlling the heating elements 300 and 219, the microcontroller 310 controls the entire operation of the apparatus 107 as will now be described. Specifically, as discussed above, the sensors 260-1 through 260-5 each provide signals to the microprocessor 310 indicating when a flag 258 of the bracket 228 of stage 212 has reached the particular sensor. The microcontroller 310 uses this sensor information to control the stepper motor 220 to move the carriage 214 in the appropriate direction, at the appropriate speed, and for an appropriate distance along the rails 218 in accordance with programmed information as is described in more detail below.

The microcontroller also includes ports 312 for receiving information provided by the keyboard 202 and soft keys, port 314 for receiving information provided by bar code scanner 211, ports 316 for controlling a disk drive 317 to read/write information to/from a data disk, and ports 318 for controlling the display 204 to display information provided by the testing or to act as a visual interface with the operator. Additionally, the microprocessor includes ports 322, 324, 326 and 328, which are coupled to an external parallel port, serial port, network port and auxiliary heater port, respectively, to send/receive data to and from external devices. The microprocessor further can provide an audio signal to speaker 332 which can inform an operator of, for example, an alarm condition.

The microcontroller 310 is powered by two power supplies 334 and 336 via a power control and distribution unit 338. The apparatus 107 further includes a fan 342 for cooling internal circuitry of the apparatus 107. The microcontroller 310 is also coupled to detector controllers 338 and 340 which control the operation of the light emitting arrays 274-1 and 274-2 and light detector devices 276-1 and 276-2 as will now be described. An AC voltage inlet port 344 provides power to the power supplies 334 and 336 when a power-on switch 346 is activated, and a circuit breaker 346 protects the apparatus against any excessive current being drawn through the AC inlet port.

After the preliminary steps discussed above with regard to FIGS. 1–3 have been performed, the tray assembly 103 including the microwell array 112 is ready to be read by the apparatus 107. The operator will enter into the apparatus 107 via the keyboard 202, soft keys or bar code scanner 211 the patient information pertaining to the samples in the tubes 108. As discussed above, each sample tube 108 will correspond to a particular microwell 116 or microwells in the tray 112. Hence, the apparatus 107 will be programmed to associate a particular microwell 116 in the tray 103 with corresponding patient information. As the information is being entered, the microcontroller 310 will store the information in a memory, and will control the display screen 204 to display interactive messages to assist the operator in entering the information.

Figure 12:
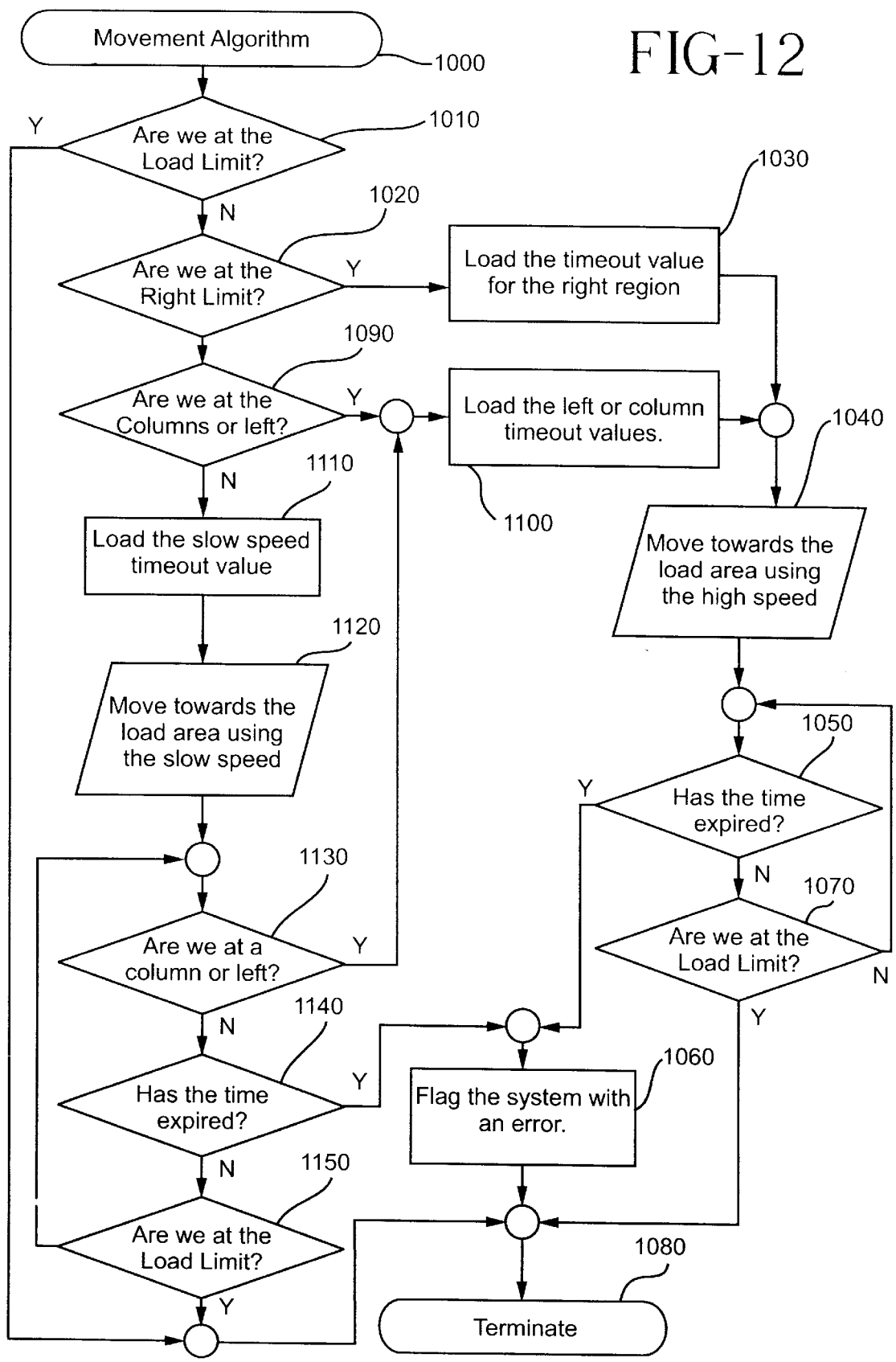
FIG. 12 is a flow chart illustrating a stage movement process performed by the apparatus shown in FIG. 5.

Before the tray assembly 103 can be placed in the tray accommodating portion 214 of the stage 212, the stage must be positioned in the loading position. Accordingly, when the operator has finished entering the patient information and enters a command via the keyboard 202 or soft keys to instruct the apparatus 107 to receive a tray assembly 103, the microcontroller 310 will control the stepper motor 220 to convey the stage 212 to the loading position. The speed at which the stage 212 is conveyed to the loading position depends on the initial position of the stage 212 along the rails 218 at the time the loading command is given. This position of the stage 212 is ascertained by the sensors 260-1 through 260-5, as will now be described with respect to the flowchart shown in FIG. 12.

When the operator has instructed the apparatus in step 1000 to position the stage 212 to receive a tray assembly 103, the microcontroller 310 will check the signals being provided by sensors 260-1 through 260-5 to ascertain whether the stage 212 is at a position along rails 218 corresponding to the position of one of those sensors. Specifically, in step 1010, the microcontroller 310 will check the signal being received from sensor 260-1 (the load limit sensor) to determine whether the stage 212 is positioned in the load position, which is approximately the position of the stage 212 as shown in FIGS. 6 and 7. As explained above, if the stage 212 is positioned in the load position, the leftmost flag 258-12 will be in the opening between light emitter 262 and light detector 264 of sensor 260-1. The signal output by sensor 260-1 will thus indicate that the stage is at the leftmost position (load position) along the rails 218. Accordingly, the microcontroller 310 will not activate the stepper motor 220 and stage 212 will not be moved. The operator will thus be permitted to open the outside door 206 of the apparatus 107 and the door 216 of the stage 212 to place the tray assembly 103 in the tray accommodating portion 214 of the stage 212.

On the other hand, if the signal provided by sensor 260-1 to the microcontroller 310 indicates that the stage 212 is not at the load position, in step 1020, the microcontroller 310 will check the signal from sensor 260-5, which is the rightmost sensor or right limit position sensor. If the signal from sensor 260-5 indicates that a flag 258, in particular, flag 258C-2 of the bracket 228 of stage 212, is present between the light emitter 262 and light detector 264 of sensor 260-5, the microcomputer 310 will ascertain that the stage 212 is at the rightmost position. It is noted that due to the manner in which sensor 260-5 is positioned with respect to the right end of carriage assembly 208, the detection of the second rightmost flag 258C-2 of the bracket 228 acts as the home position indicator. It is noted that the sensor 260-5 is positioned lower that the bottom edge of flag 258C-1, so it does not detect that flag. However, flag 258C-2 is made longer so that the sensor 260-5 can detect the presence of that flag. It is further noted, however, that the sensor 260-5 can be repositioned so that the rightmost flag 258C-1 or, for that matter, any of the flags 258, is detected as the load position indicator flag which indicates that the stage 212 is at the load position. Likewise, sensor 260-1 need not be positioned to detect the leftmost flag 258-12 as indicating that the stage 212 is at the loading position, but rather, could be positioned to detect any of the flags 258 as providing the load position indication.

Once it is determined that the stage 212 is at the home position, in step 1030, the microcontroller 310 will then load an appropriate "time out value" in memory (not shown). The "time out value" is a value representing the amount of time that should elapse when the stage 212 is moved from the rightmost position on the rails 218 to the leftmost or load limit position on the rails 218. This time is, for example, 8 seconds in the embodiment, but can be any value depending on the speed at which the stage 212 is conveyed. The microcontroller 310 will thus be able to ascertain whether an error has occurred in the conveyance of the stage 212 by comparing the time it takes for the stage 212 to reach the left load limit position versus the time out value.

That is, after setting the time out value in step 1030, the microcontroller 310 will control the stepper motor 220 in step 1040 to move the stage along rails 218 at a certain speed in a direction toward the load limit position. The microcontroller 310 monitors the time that is elapsing while the stage 212 is being conveyed. If the microcontroller determines in step 1050 that the amount of time that has elapsed exceeds the time out value, the microcontroller 310 will proceed to step 1060 where it will issue an error message to be displayed on the display screen 204, which will alert the operator that an error in the conveying mechanism may have occurred.

As long as the conveying time that has elapsed does exceed the time out value, the microcontroller will continuously check the signal being provided by the load limit sensor 260-1 to determine whether the stage 212 has reached the load limit position. The microcontroller 310 will continue controlling the stepper motor 220 to convey the tray 212 toward the load limit position, and will continuously monitor and compare the conveying time that has elapsed to the time out value. Assuming that the elapsed time does not exceed the time out value, when the stage reaches the load position in step 1070 as indicated by the signal provided by load limit sensor 260-1 to the microprocessor 310, the microcontroller proceeds to step 1080 to terminate the conveyance of the stage 212 by the stepper motor 220. Accordingly, the operator is then permitted to open the door 202 of the apparatus and the door 216 of the stage 212, and can insert the tray assembly 103 in the tray accommodating portion 214 of the stage 212.

Referring back to step 1020, if the right limit sensor 260-5 provides a signal to the microcontroller 310 indicating that the tray is not present at the home position, the microcontroller will determine whether the signals provided by any of sensors 260-2, 260-3 or 260-4 indicate the presence of the stage 212 at a location along the rails 218 corresponding to the position of either of those sensors. If, in step 1090, the microcontroller determines that the stage 212 is at the position of either of the sensors 260-3 or 260-4 (the light bar sensors, indicated as "columns" in step 1090), the microcontroller 310 will load an appropriate time out value in memory. Naturally, that time out value is shorter than the time out value used if the stage 212 is determined to be at the right limit position as indicated by sensor 260-5.

The microprocessor then repeats steps 1040 through 1070 described above using this column time out value as the maximum time allotted for the stage 212 to be conveyed from its detected position on the rails 218 to the load position. If the time that has elapsed during the conveying of the stage 212 to the load position exceeds this time out value, the microcontroller 310 will issue an error signal in step 1060. However, if the stage 212 reaches the load position within the allotted amount of time, the microcontroller 312 will stop the stepper motor 220 from conveying the stage 212.

Alternatively, if in step 1090 the microcontroller 310 determines from a signal output by sensor 260-2 that the tray is at a position along rails 218 corresponding to that sensor (the "left" position, which is the leftmost position in the oven 246), the processing will proceed to step 1100 where the microcontroller 310 will load in memory a time out value appropriate for that detected position. That time out value will be smaller than the column time out value, because the distance that the stage 212 has to travel between the sensor 260-2 and the load position is less than the distance that the stage 212 would have to travel from the column detectors 260-3 and 260-4, or from the right limit sensor 260-5. The microcontroller 310 then repeats steps 1040 through 1070 as described above using this appropriate time out value as the maximum allotted time during which the stage 212 can be conveyed from the position corresponding to sensor 260-2 to the load position. If the elapsed time exceeds the time out value, the microcontroller will generate an error signal in step 1060. However, if the stage 212 reaches the load position before the allotted time period has expired, the microcontroller 310 will control the stepper motor 220 to stop conveying the stage 212, and the operator will be permitted to load a tray assembly 103 into the stage 212.

If, however, in step 1090, the signals provided by detectors 260-2, 260-3 or 260-4 indicate that these detectors have not detected the presence of the stage 212, the microcontroller 310 will not be able to ascertain exactly where the stage 212 is positioned along the rails 218. Accordingly, in step 1110, the microcontroller will load a slow speed time out value in memory, and in step 1120, will control the stepper motor to convey the stage 212 toward the load position at a slow speed which is slower than the speed at which the stage. That is, if the stage 212 were positioned along the rails 218 between sensor 260-2 and the load limit sensor 260-1 and thus, close to the load position, it would not be necessary to move the stage 212 at the high speed to the load position. By moving the stage 212 at a high speed when it is close to the load position, the conveying mechanism can be damaged if, for example, the stepper motor 220 has to abruptly stop when the stage 212 quickly reaches the load position. Since the microcontroller 310 cannot determine whether the stage 212 is between sensors 260-2 and 260-1 and thus close to the load position, as a precautionary measure, the microcontroller 310 will move the stage 212 at a slow speed until the actual position of the stage is determined.

When the stage 212 is being conveyed at the slow speed, if the sensors 260-2, 260-3 or 260-4 provide a signal to the microcontroller 310 in step 1130 indicating the presence of the stage 212, the microcontroller 310 will proceed to step 1100 and load the appropriate time out value based on the detected position of the stage 212. The microcontroller 310 will then continue with steps 1040–1070 and move the stage at the faster speed, because the microcontroller 310 will have ascertained that the stage 212 is close to the load position.

If the stage 212 is being moved and it has not been detected by sensors 260-2, 260-3 or 260-4, the microcontroller will determine in step 1140 whether the amount of conveying time that has elapsed has exceeded the slow speed time out value. If this has occurred, the microcontroller 310 will ascertain that an error exists in the conveying mechanism and will issue an error signal in step 1060 and terminate the operation in step 1080.

However, if the elapsed time has not exceeded the maximum allotted time indicated by the slow speed time out value, the microcontroller 310 will determine in step 1150 whether the stage 212 has reached the load limit sensor 260-1 and thus, is at the load position. If the stage has reached the load position, the microprocessor will continue to step 1080 and terminate the movement of the stage 212. At this time, the stage 212 can be accessed by an operator in the manner described above. However, if in step 1150 the microcontroller 310 determines from the signal provided by sensor 260-1 that the stage 212 has not reached the load position, the processing will return to step 1130 and repeat the above steps as appropriate until either the maximum allotted time has elapsed or the stage 212 has reached the load position.

Although the stage 212 is described above as being conveyed at a high speed or a low speed, the speed at which the stage 212 is conveyed can further be varied depending on the position of the stage 212 along the rails 218. That is, the microcontroller 310 can change the conveying speed, if desired, every time the stage 212 reaches a particular sensor 260-2 through 260-4, until the movement is finally stopped when the stage 212 reaches the sensor 260-1.

Figure 13:
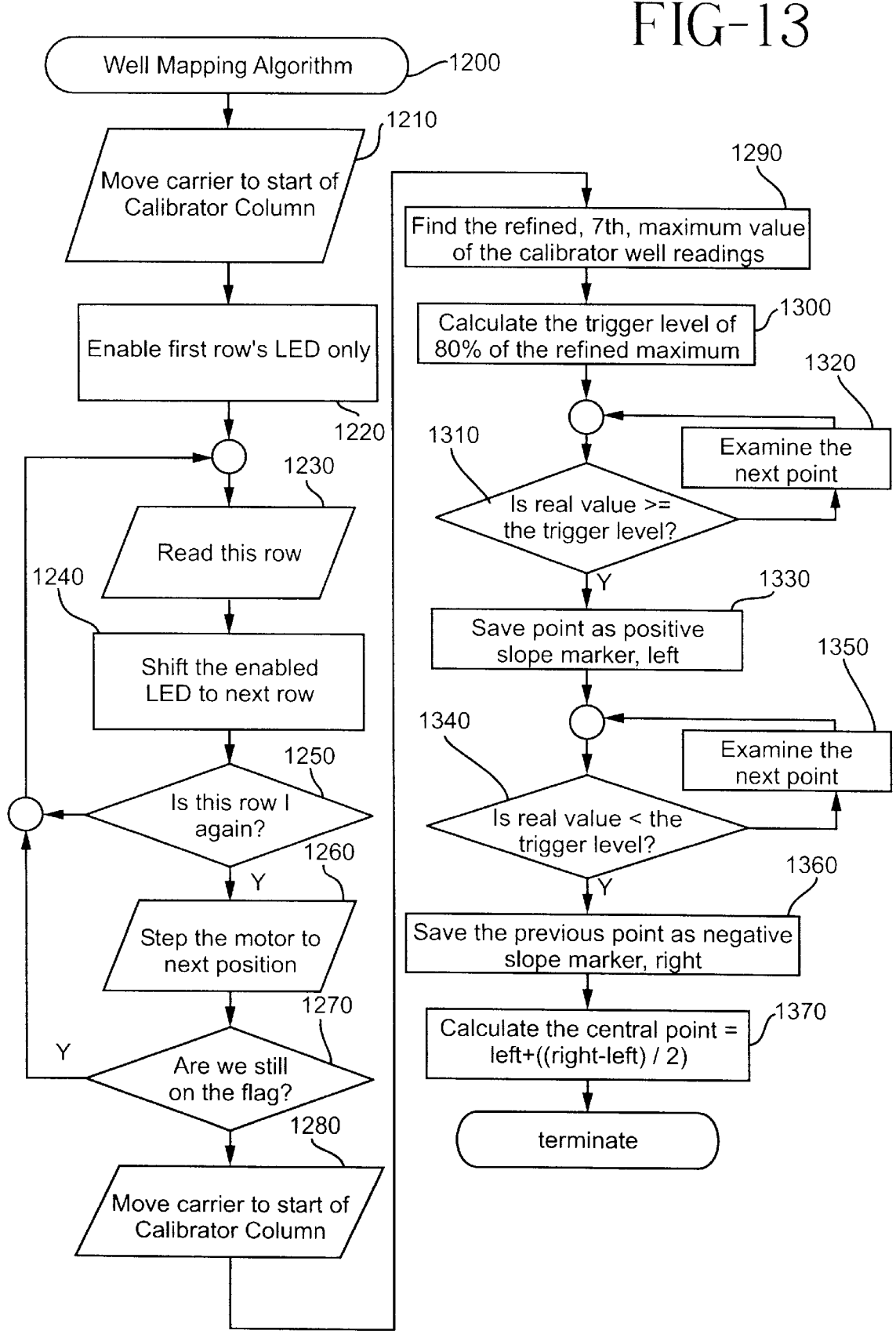
FIG. 13 is a flow chart illustrating the steps of a microwell mapping algorithm performed by the apparatus shown in FIG. 5.

Before or after the stage 212 has been moved to the load position in the manner described above and a tray assembly 103 has been loaded in the stage 212, the apparatus 107 will operate to map the positions of the calibration wells 116C on the stage 212 and accordingly, the positions of the individual wells 116 of the well array 112, so that the light emitting arrays 274-1 and 274-2 can be controlled to emit light when the wells 116 are positioned appropriately over their light corresponding emitting/detecting ports 274. The well mapping process that the apparatus 107 performs will now be described with reference to the flow chart shown in FIG. 13. It is noted that since this embodiment includes two light sensor bars 270-1 and 270-2, the following mapping procedure must be repeated for each sensor bar. However, as will be described below, if only one type of read is performed, only one sensor bar (usually sensor bar 270-1) will be active. Accordingly, for exemplary purposes, the well mapping procedure will be described in detail with respect to sensing bar 270-1.

When the well mapping process begins in step 1200, the microcontroller 310 controls the stepper motor 220 to move the stage 212 from the load position as shown in FIG. 7 to a position where the front flag 258C-1 will be detected by the sensor 260-4. When the stage 212 is positioned in that position, the apparatus 107 is ready to begin mapping the first column 213-1 of calibration wells. It is noted that the first flag 258C-1 is aligned with or essentially aligned with the first column 213-1 of calibration wells. This first flag 258C-1 will thus be used as a position indicator which indicates the position of the first column of calibration wells 213-1 with respect to the light bar 270-1.

As indicated in step 1220, the first LED 275-1 will be energized for a period of time as controlled by the controller 320 to emit light through its corresponding optical fiber 280-1 and out of its corresponding light emission/detection port 272 of the light bar 270-1. As discussed above, each of the calibration wells 116C-1 through 116C-8 in the first column 213-1 of calibration wells includes a calibration dye made of a material that fluoresces when excited by light having a particular wavelength. When the LED 275-1 has been energized and de-energized, the photodetector 276-1 will be controlled by the controller to detect the 310 light emitted from the material in the well 116C-1 due to the excitation by the light from LED 275-1. The light emitted by that luminescence reaches the photodetector 276-1 by passing through the light emitting/detecting port 272-1 and corresponding optical cable 282-1. The photomultiplier tube 276-1 provides an electrical signal indicative of the intensity of the detected light to the microcontroller 310, and the microcontroller 310 will store that signal in memory.

After a predetermined period of time during which the photomultiplier 276-1 detects the light illuminating from the material in the well 215-1, the microcontroller 310 will become ready in step 1240 to energize the next LED 275-2 in the light emitting array 274-1. However, prior to energizing that LED, the microcontroller 310 will determine in step 1250 whether that LED is the first LED 275-1. In other words, in step 1240, the microcontroller 310 updates a count of the LEDs to be energized from 1 to 2, thus indicating that the second LED in the array of LEDs 275-1 through 275-8 is to be energized. However, since there are only 8 LEDs in the array, the count will not exceed 8, but rather, will return to 1 after 8.

If the count indicates that LED to be energized is not the first LED 275-1, the microcontroller 310 will return to step 1230 and energize LED 275-2. The photomultiplier 276-1 will be allowed to detect any light that may be emitted from the luminescent material present in calibration well 116C-2. After that predetermined detection time has elapsed and the photomultiplier tube 276-1 has provided a signal to the microcontroller 310 indicative of the light intensity emitted from calibration well 215-2, the microcontroller 310 will update the count of the LED to be energized to become ready to energize the third LED 275-3. As with the second LED 275-2, prior to energizing the LED 275-3, the microcontroller 310 will determine whether the count has returned to 1. Since the LED count has not been returned to 1 in this case, the microcontroller 310 will return to step 1230 and the above process will be repeated for the third LED 275-3.

After all 8 LEDs 275-1 through 275-8 have been energized, when the microcontroller updates its LED count in step 1240, the microcontroller 310 will determine that the next LED to be energized is indeed the first LED 275-1 (the count has returned to 1). Accordingly, the microcontroller 310 will proceed to step 1260, where it will control the stepper motor 220 to move the stage 212 by one step in the direction toward the home position. In step 1270, the microcontroller 310 will check the signal being provided by sensor 260-4 to determine whether the sensor is still detecting the presence of flag 258C-1. If the sensor 260-4 is still detecting the presence of flag 258C-1, then the processing will return to step 1230 and the 8 LEDs 275-1 through 275-8 will be energized sequentially in the manner described above.

This process continues until the microcontroller 310 has controlled the stepper motor 220 to have moved the stage 212 far enough so that the flag 258C-1 no longer interrupts the transmission of light from light emitter 262 to light detector 264 in sensor 260-4. Accordingly, sensor 260-4 will provide a signal to the microcontroller 310 indicating that the flag 258C-1 has passed the sensor 260-4. In this embodiment, the stepper motor 220 is configured to move the stage 212 approximately 250 steps for each flag 258. Hence, when the sensor 260-4 indicates that the flag 258C-1 has passed, approximately 250 readings will have been taken for each well in the calibration column 213-1.

The microcontroller 310 then proceeds to step 1280 where it controls the stepper motor 220 to move the stage 212 back to the position along rails 218 where flag 258C-1 begins to be detected by sensor 260-4 (the position of the flag 258C-1 as in step 1201). The stage 212 will be maintained at this position, and the microcontroller 310 will proceed to step 1290 to perform the well mapping procedure.

In this embodiment, the microcontroller 310 is programmed to ignore the 6 highest intensity readings for each well. That is, as discussed above, when the LED associated with a particular well is energized to radiate light into that well, the calibration material in the well will be excited by that radiated light and emit light in response. The intensity of the emitted light will typically be at a maximum when the center of the bottom of the well is positioned directly over its light emitting/detecting port 272. This occurs because the light radiated by the LED passing through the light emission/detection port 272 will enter the well most directly, and the light being emitted from the well will enter the light emission/detection port 272 most directly. However, due to inconsistencies in the well, the calibration material, and so on, a false maximum intensity may be detected at a position other than the center of the well. To reduce the affect of these aberations, the microcontroller 310 is programmed to ignore the 6 highest intensity readings. However, any other type of error detection process or method could be used.

In step 1300, the microcomputer 310 will calculate a "trigger level" which is a reference level equal to 80% of the maximum intensity value determined in step 1290 after the 6 highest intensity values have been ignored. This 80% trigger level value is used to locate the center of the well.

Figure 14:
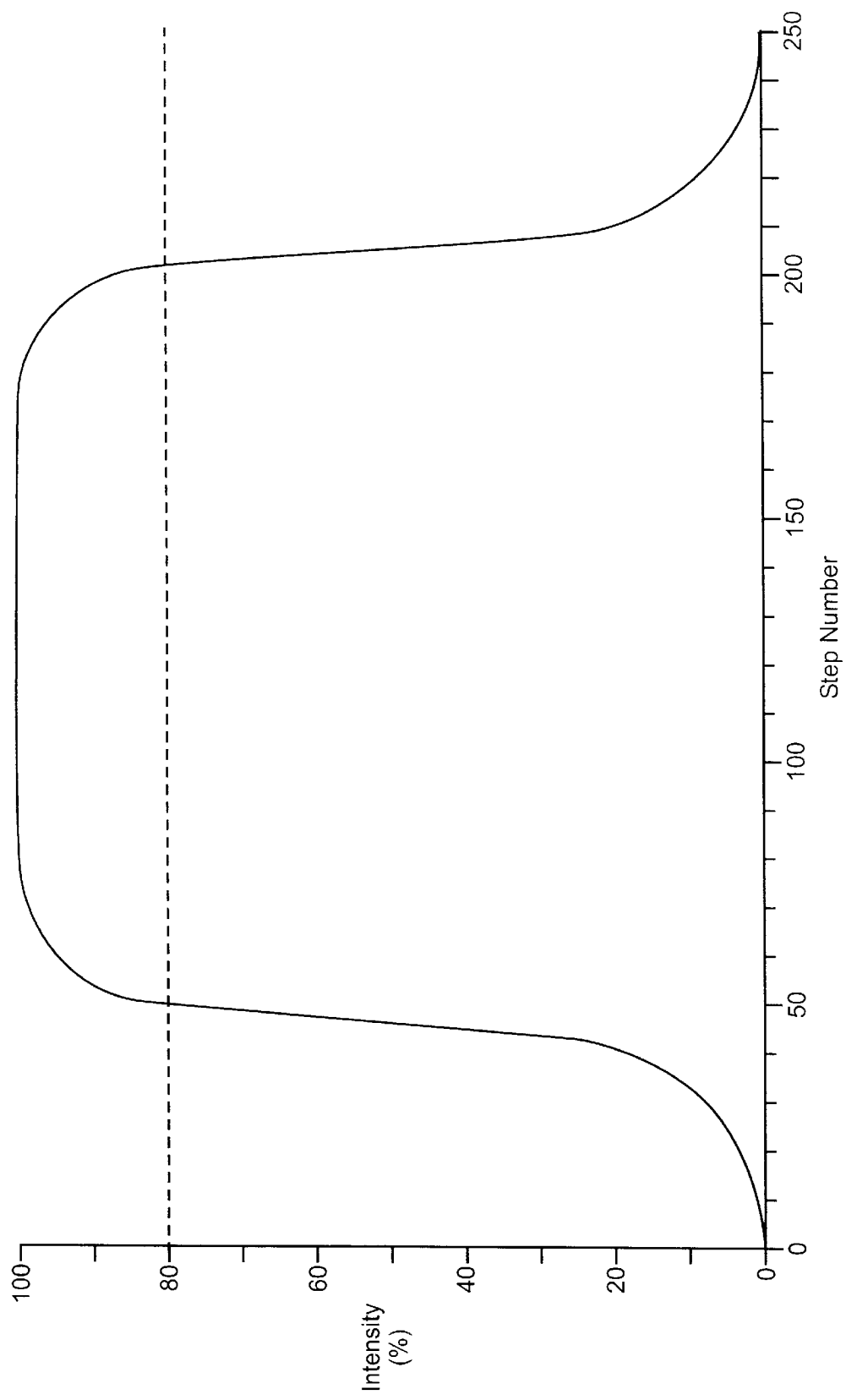
FIG. 14 is a graph showing detected intensity values at detection points taken along the bottom of a single microwell of the microwell array shown in FIG. 4.

As shown in FIG. 14, the plurality of readings for any particular well form a bell shaped curve when plotted with intensity level on the Y axis and the number of the step at which the reading was taken on the X axis. As illustrated, the first several steps are taken when the flag is first detected by the sensor 260-4. Since the flag is slightly larger than the direction of the well, the well is offset from the center of the light emitting/detecting port 272, and for the reasons described above (e.g., indirect light emission and detection), the detected intensity of the emitted light is very low. However, as the well becomes more and more centered with its respective light emitting/detecting port 272, the detected intensity increases to a maximum. The microcontroller 310 reads from the memory the stored intensity value for each step, beginning with step 1, compares the stored intensity value with the 80% trigger level in step 1310 of the processing. If the intensity level measured of the compared reading is less than the 80% trigger level, the microcontroller 310 will continue to compare the readings, step-by-step until an intensity level is detected which is greater than or equal to the 80% trigger level. In this example, the intensity value taken at the 50th step is equal to the 80% trigger level. Incidentally, after detecting an intensity value which is equal to or greater than the trigger level, the next several intensity values for the next several steps will also be compared with the 80% trigger level to assure that that detected value is not an aberation such as an intensity spike in the bell curve.

After it has been confirmed that the value equal to or greater than the trigger level is genuine, that step number corresponding to that intensity value is stored in memory as the left hand marker in step 1330. The intensity values for the remainder of the steps will be checked one by one in steps 1340 and 1350 until one of those intensity values is detected as being less than the trigger level. In this example, the intensity value at step 107 is less than the 80% trigger level.

When it has been determined that that intensity value is genuine (e.g. by detecting that intensity value for the next several steps are below the trigger value), the step having that intensity value will be stored as the right hand marker in step 1360 of the processing. The microcontroller 310 will then perform the following calculation in step 1370 to calculate the midpoint of the well, as represented by the number of steps that the stepper motor must step from the point when the 258 corresponding to column the well has first been detected by the sensor 260-4 corresponding to the light sensor bar 270-1:

Central Point=Left+((Right-Left)/2)

In this example, the central point is detected to be step 125. Hence, the microcontroller 310 has determined that when a flag 258 is initially detected by sensor 260-4 corresponding to the light sensor bar 270-1, the microcontroller 310 must control the stepper motor 220 to move another 125 steps in order to center the wells 116 in the column corresponding to that flag 258 directly above the centers of light emitting/detecting ports 272.

This calculation process described in steps 1290 through 1370 can be repeated for each of the 8 wells 116 in the calibration column 215-1. Then, if desired, an average of those number of steps can be taken to get an average number of steps that is necessary to center the column of wells 215-1 with the corresponding light emitting/detecting ports 272 of the light bar 270-1 corresponding to sensor 260-4.

Additionally, as illustrated, the stage 212 includes 4 columns 213-1 through 213-4 of calibration wells 116C. Hence, the above process can be repeated for each of the 4 columns of calibration wells 116 and, if desired, an average value can be taken to thus accurately determine the number of steps necessary to center each of the columns of wells over the light emitting/detecting ports 272 when the flags corresponding to those wells have been detected. It is further noted that when the tray assembly 103 is placed in the stage 212, the position of each of the 12 columns of wells in the well array 112 will correspond to a respective flag 258. Since those 12 flags and the 4 calibration flags have the same or substantially the same width, the centers of the wells 116 in each column of wells can be centered directly over the corresponding light emitting/detecting ports 272-1 through 272-8 by controlling the stepper motor to move in the appropriate number of steps as calculated in the above process.

Additionally, if desired, a test microwell array 112 having 96 test wells (the number corresponding to that of an actual microwell array 112), each of which includes a calibration material, can be loaded in the stage 212. The above well mapping process can then be repeated for each column of wells (12 columns of 8 wells each) to obtain a more accurate mapping of the 8×12 well array and, in particular, amore accurate indication of the centers of the wells in each column with respect to the corresponding flag for that column.

As stated above, the above well mapping process must be repeated for the second light sensor base 270-2 if that sensor bar 270-2 is going to be used to read the microwell array 112. In this event, the calibration wells 116C and hence all the wells 116, are mapped by using the sensor 260-3 whose position corresponds to that of light sensor bar 270-2.

Figure 15:
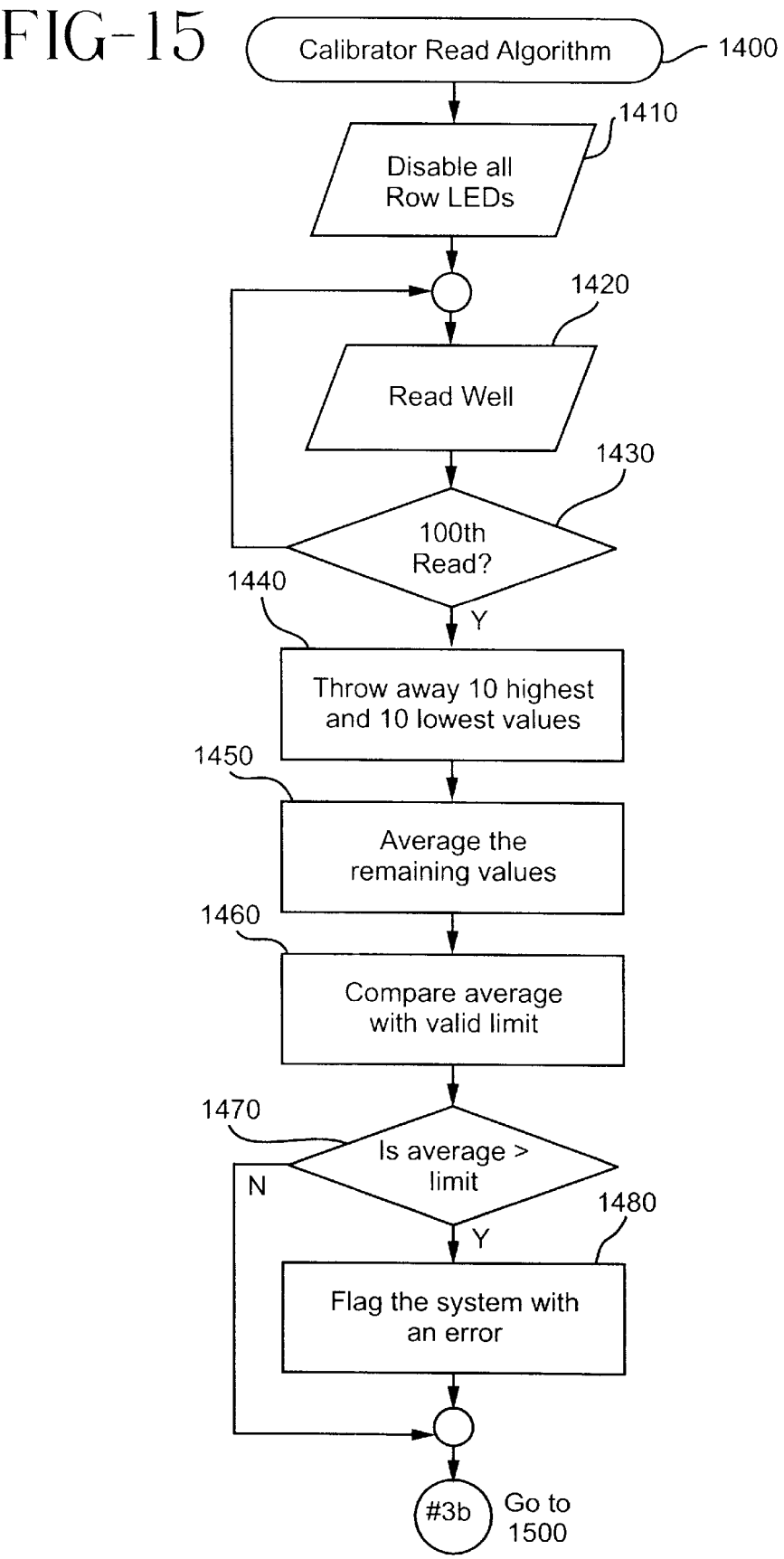
FIG. 15 is a flow chart showing steps of a dark read calibration process performed by the apparatus shown in FIG. 5.

The apparatus 107 will further operate to verify the integrity of the light emitting arrays 274-1 and 274-2 and to set the control voltages of the photomultiplier tube 276-1 and 276-2 at the appropriate levels. Specifically, as shown in FIG. 15, beginning in step 1400, microcontroller 310 will control the apparatus to perform a dark reading to assure that no stray light is entering the light emitting/detecting ports 272 through, for example, a hole in the wall of the oven 246. To perform this dark operation on the light array 274-1 and photomultiplier tube light detection 276-1, the microcomputer 310 in step 1410 disables all of the LEDs 275-1 through 275-8 in the LED array 274-1. The light detector 276-1 is controlled to take 100 measurements in steps 1420 and 1430, and stores the values of these 100 measurements in memory so that an average value can be calculated.

Specifically, in step 1440, the microcomputer 310 will ignore the ten highest and ten lowest readings to eliminate any erroneous readings. In step 1450, the microcomputer will average the 80 remaining readings, and in step 1460, compare the average intensity value with a limit intensity value. If the microcontroller 310 determines in step 1470 that the average value is greater than the limit value, the processing will proceed to step 1480 where the microcontroller 310 will control the display screen to display an error message. This error message indicates, for example, that stray light is entering the oven 246 and thus is being detected by the detector 276-1 through the light emitting/detecting ports 272. However, if the average value has not exceeded the limit value, the microcontroller 310 will determine that little or no stray light is being detected by the detector 276-1, and the processing will proceed to calibrate the control voltage of the photomultiplier tube light detector 276-1. The above dark reading process also can be repeated for the light array 274-2 and light detector 276-2 if those components are to be used in reading the well array 112.

Figure 16:
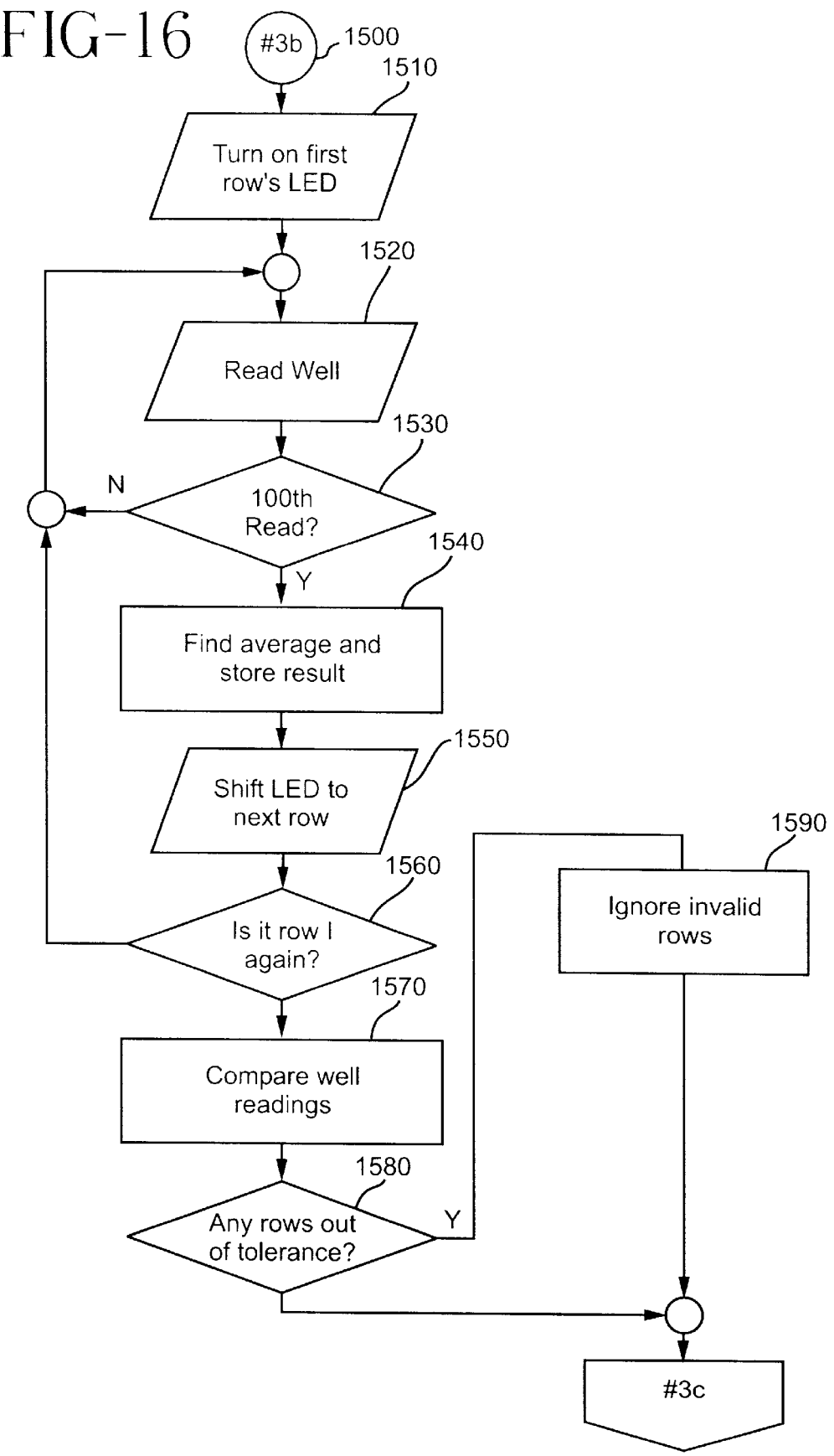
FIG. 16 is a flow chart showing the steps of an optical reader integrity check process performed by the apparatus shown in FIG. 5.

After the dark read calibration process is completed, the microcontroller 310 will begin calibrating light detectors 276-1 and 276-2. As shown in FIG. 16, in step 1500, the microcontroller 310 will center the first column 215-1 of calibration wells 116C above the light emitting/detecting ports 272 of light sensor bar 270-1 by controlling the stepper motor to move the appropriate amount of steps once the flag 258C-1 associated with the column 215-1 of wells is detected by sensor 260-4. In step 1510, the microcontroller 310 will energize LED 275-1 associated with the first well 116C-1 in the column 215-1 so that the calibration material in the well 116C will be excited and thus emit light. In steps 1520 and 1530, the detector 276-1 will be controlled by the microcontroller 310 to take 100 readings from the well 116C-1 or, in other words, detect 100 intensity values of the light being emitted from the material in the well during a period when the material has been excited by the light from the LED 275-1. After the 100 readings have been performed for that particular well, the microcontroller 310 takes an average intensity value in step 1540. The microcontroller 310 then energizes the next LED in the LED array (LED 275-2) and 100 readings from the second well are taken and stored in memory. The process in steps 1520 through 1560 is repeated until 100 readings have been taken from each well 116C-1 through 116C-8 in calibration column 215-1. The processing then continues to step 1570 where the microcontroller 310 comprises the 8 fluorescent intensity valves (i.e., 1 for each well with each other to determine if any are significantly different from the rest. If any of the intensity valves have been determined to be significantly different from the others, the microcontroller 310 will ascertain that a defect exists in the optical components associated with the light emitting/detecting port 272 that was used to read that well (e.g., an LED is burned out, a fiber optic cable is damaged, and so on). The microcontroller 310 can then control the screen display 204 to display an error message (e.g., "Well No. 3 Reader is Defective"), and disable that particular well reader in step 1590 (e.g., LED 275-3 would be disabled, and readings would be taken for wells 1, 2 and 4–8 in any of the columns).

The microcontroller 310 will then adjust the voltage of the light detector 276-1 photomultiplier tube so that the photomultiplier tube will output voltage signals the desired levels when detecting the radiation emitted from the wells 116.

Figure 17:
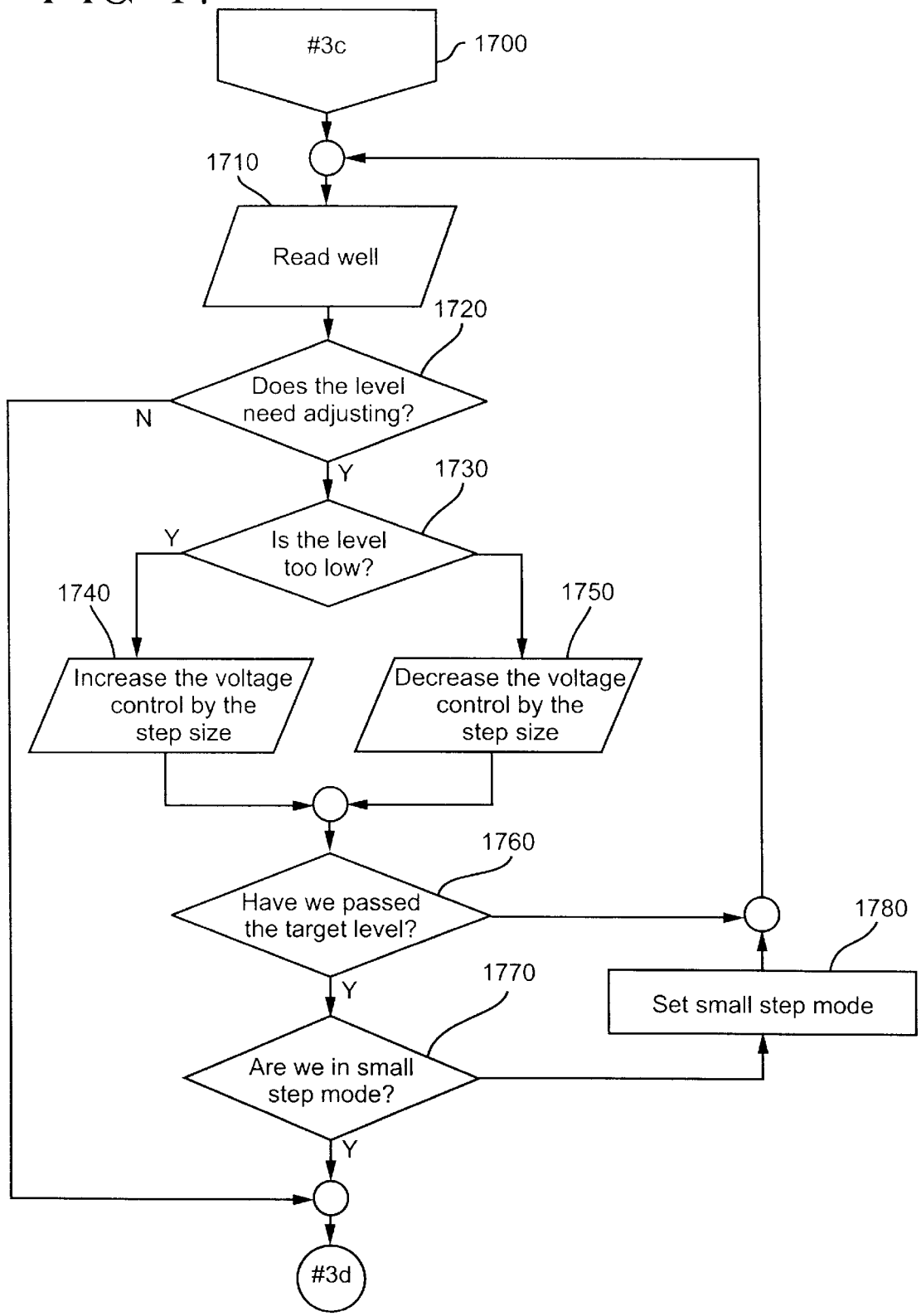
FIG. 17 is a flow chart showing the steps of a photomultiplier tube light detector control voltage adjusting process performed by the apparatus shown in FIG. 5.

As shown in FIG. 17, in step 1700, the calibration column 215-1 is aligned for reading by the light bar 270-1. The microcontroller 310 controls the LED corresponding to the well 116C that provided the highest average reading in step 1570 (FIG. 16) to illuminate. The light emitted by that LED will radiate into the well 116C, and the material in the well 116C will fluoresce light in response.

In step 1710, the light detector 276-1 is controlled to detect the light being emitted from that well 116C, and will compare the detected value with a predetermined expected target value. If the microcontroller 310 determines in step 1720 that the signal output by the light detector 276-1 is at the desired level, the microcontroller 310 will have determined that the control voltage of the photomultiplier tube light detector 276-1 does not need to be adjusted. However, if the level of the signal output by the photomultiplier tube light detector 276-1 is too low, the control voltage of the photomultiplier tube light detector 276-1 will be increased by a predetermined increment in step 1740. On the contrary, if the output voltage is determined in step 1730 to be too high, the photomultiplier tube voltage will be decreased by a predetermined increment in step 1750.

The microcontroller 310 will then determine in step 1760 whether the output signal by the photomultiplier tube has passed the expected target level due to the increasing or decreasing of the voltage in steps 1740 or 1750, respectively. If the output voltage has not passed the target level, the processing will return to step 1710 and the well will be read again.

If in step 1720, the microcontroller 310 determines that the output voltage of the photomultiplier tube is at the appropriate level, the processing will end. However, if the microcontroller 310 determines that the output voltage is not at the desired level, the processing in steps 1730 through 1760 will be repeated. If the microcontroller 310 then determines that the output voltage of the photomultiplier tube has passed the target level due to the increase or decrease of the photomultiplier tube voltage in steps 1740 or 1750, respectively, which have been repeated, the processing will continue to step 1770 where the increment at which the photomultiplier tube voltage is increased or decreased is reduced in step 1780, and the processing will then return to step 1710 and repeat steps 1710 through 1760 as described above using this smaller step of increment or decrement. This will result in the output voltage of the photomultiplier tube light detector to be close to the desired level as possible.

Figure 18:
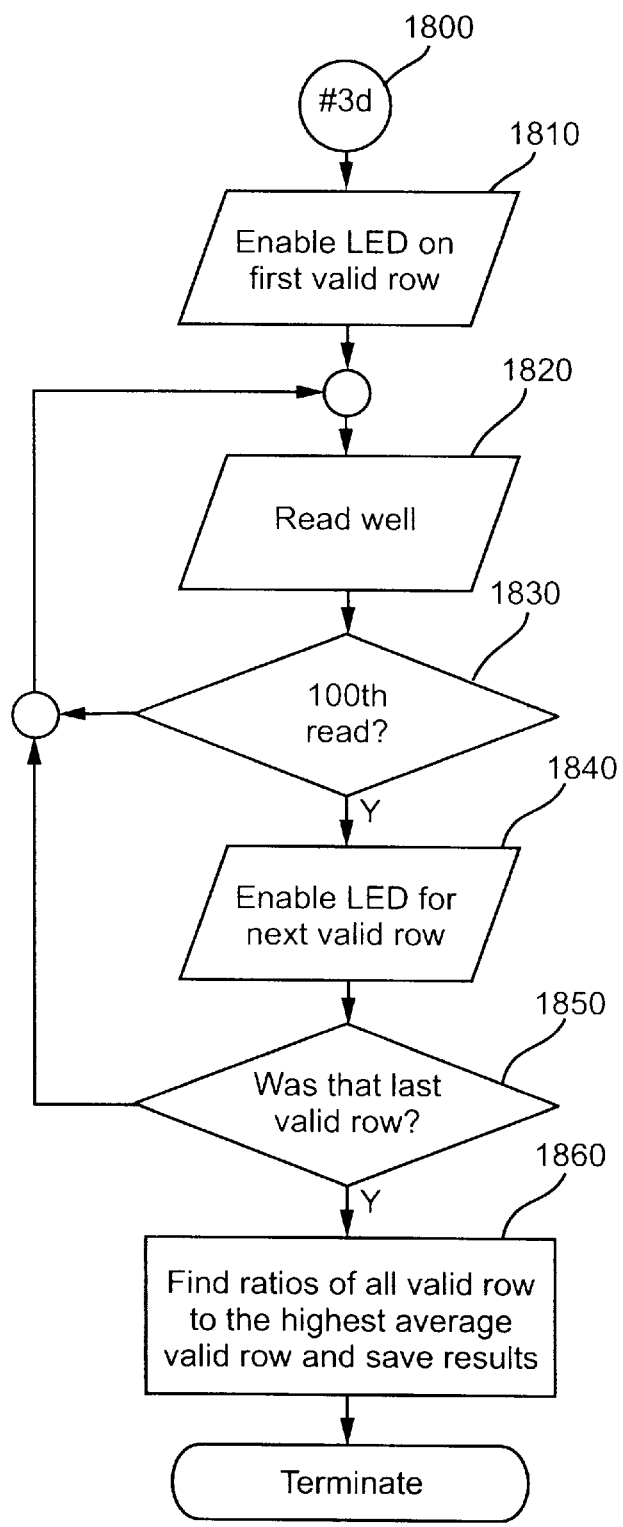
FIG. 18 is a flow chart showing the steps of a further photomultiplier tube light detector control voltage adjusting process performed by the apparatus shown in FIG. 5.

The microcontroller 310 can then proceed to reread all of the valid wells 116C in calibration column 215-1 again as illustrated in FIG. 18. As stated above, if the readings from any of the wells 116C have been found to be erroneous in the previous processing steps described in FIG. 16, the microcontroller 310 will ignore those wells. When this additional calibration processing begins in step 1800, the microcontroller 310 will energize the LEDs corresponding to the valid wells 116C in the calibration column 215-1 in the sequential manner described above, and control the light detector 276-1 to take 100 readings of each valid wells (steps 1810–1850). The microcontroller 310 can average those values in step 1860, and store an average value in memory. Accordingly, the microcontroller 310 can adjust the control voltage of the photomultiplier tube light detector 276-1 based on this average value, if desired.

It is noted that in this embodiment, the stage 212 includes 4 columns 215-1 through 215-4 of calibration wells. In such an arrangement, the microwells 116C in two columns (e.g., 270-1), and the microwells 116C in the remaining two columns (e.g., 215-3 and 215-4) include calibration material that fluoresces when energized with light having a wavelength such as the light emitted from one of the light sensor bars (e.g., 215-3 and 215-4) including micro wells containing material that fluoresces when irradiated with light emitted from the other light sensor bar (e.g., 270-2). In this event, the calibration columns 215-1 and 215-2 are used to perform calibration with respect to light sensor bar 270-1, and calibration columns 215-3 and 215-4 are used to perform calibration with respect to light sensor bar 270-2. It is further noted that the calibration material in one of the calibration columns associated with each sensor bar can be a positive type demonstrative of a positive reading; and the wells of the other calibration columns can include negative calibration material demonstrative of a negative reading. Hence, the above processing shown in FIGS. 15–18 can be repeated for each column, if desired. Also, although the processing is described for light sensor bar 270-1 (light emitter array 274-1 and light detector 276-1), the above process is repeated for the light emitter array 274-2 and light detector 274-2 and light detector 276-2 associated with light sensor bar 270-2, if light sensor bar 270-2 is to be used to take readings of the microwell array 112.

Figure 19:
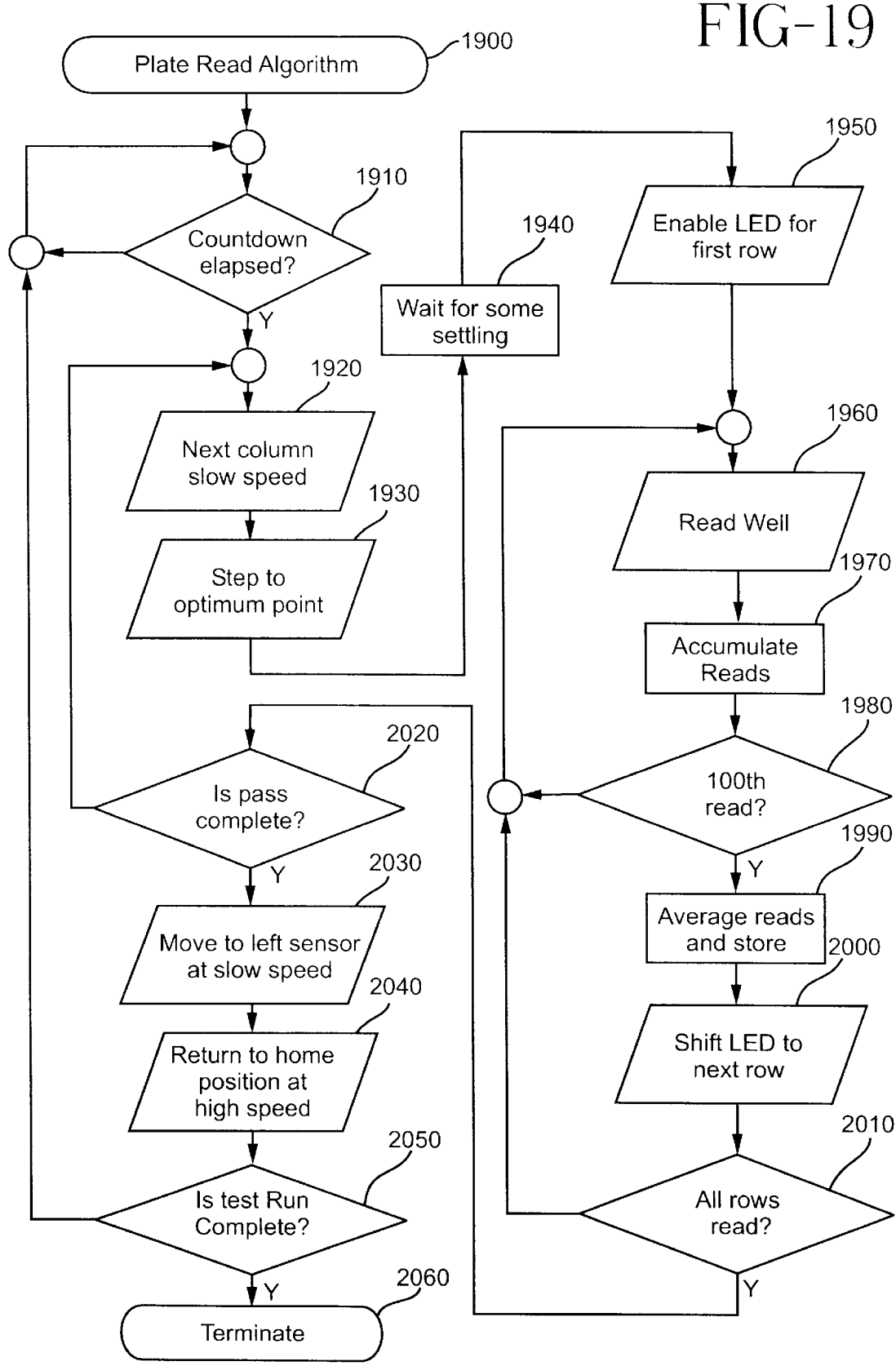
FIG. 19 is a flow chart showing the steps of a microwell reading process performed by the apparatus shown in FIG. 5.

When all of the above calibration operations have been completed, the stage 212 is conveyed along rails 218 to the home position corresponding to sensor 260-5 to begin the well reading process, which will now be described with reference to the flowchart in FIG. 19 and the sequence diagrams in FIGS. 20–25.

Figure 20:
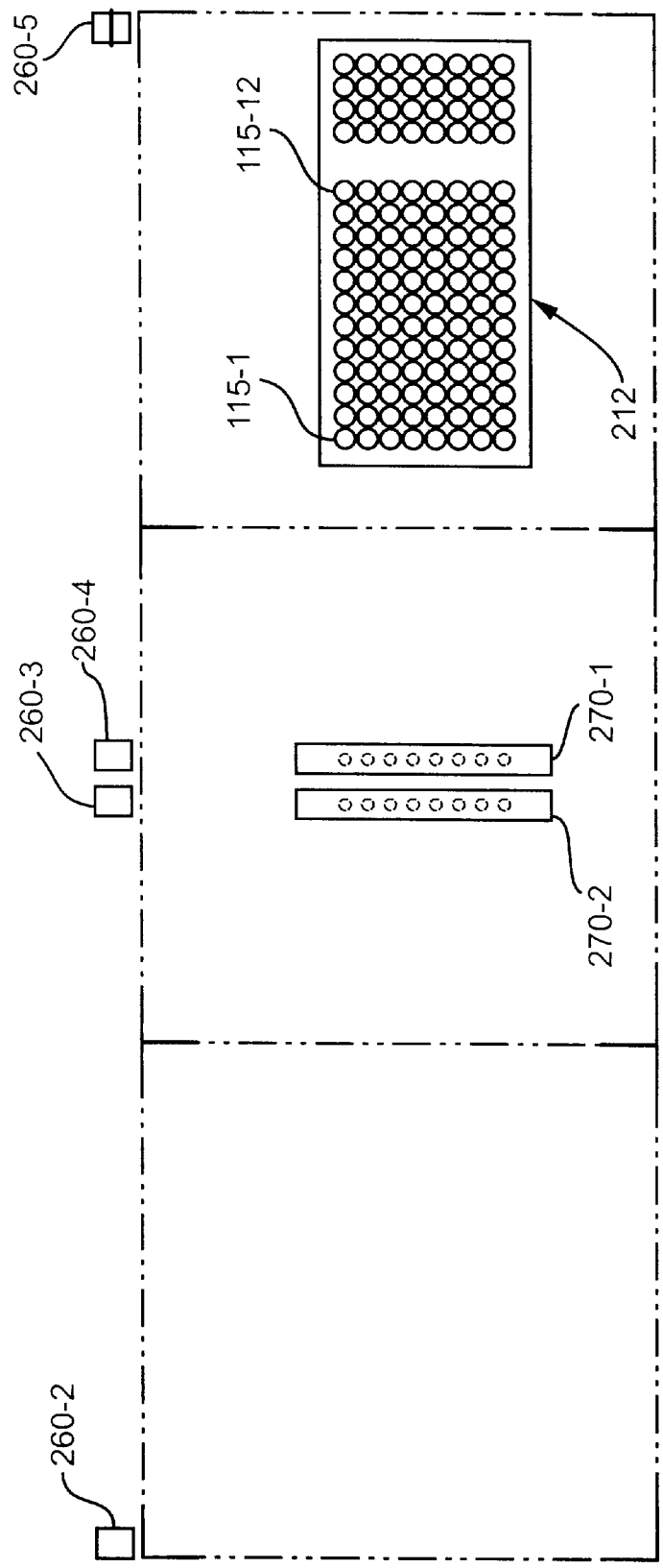
FIG. 20 is a diagram illustrating the relationship between the positions of the microwell array, housed in the stage, and the light sensor bars of the apparatus shown in FIG. 5 when the stage is positioned at the home position.
Figure 21:
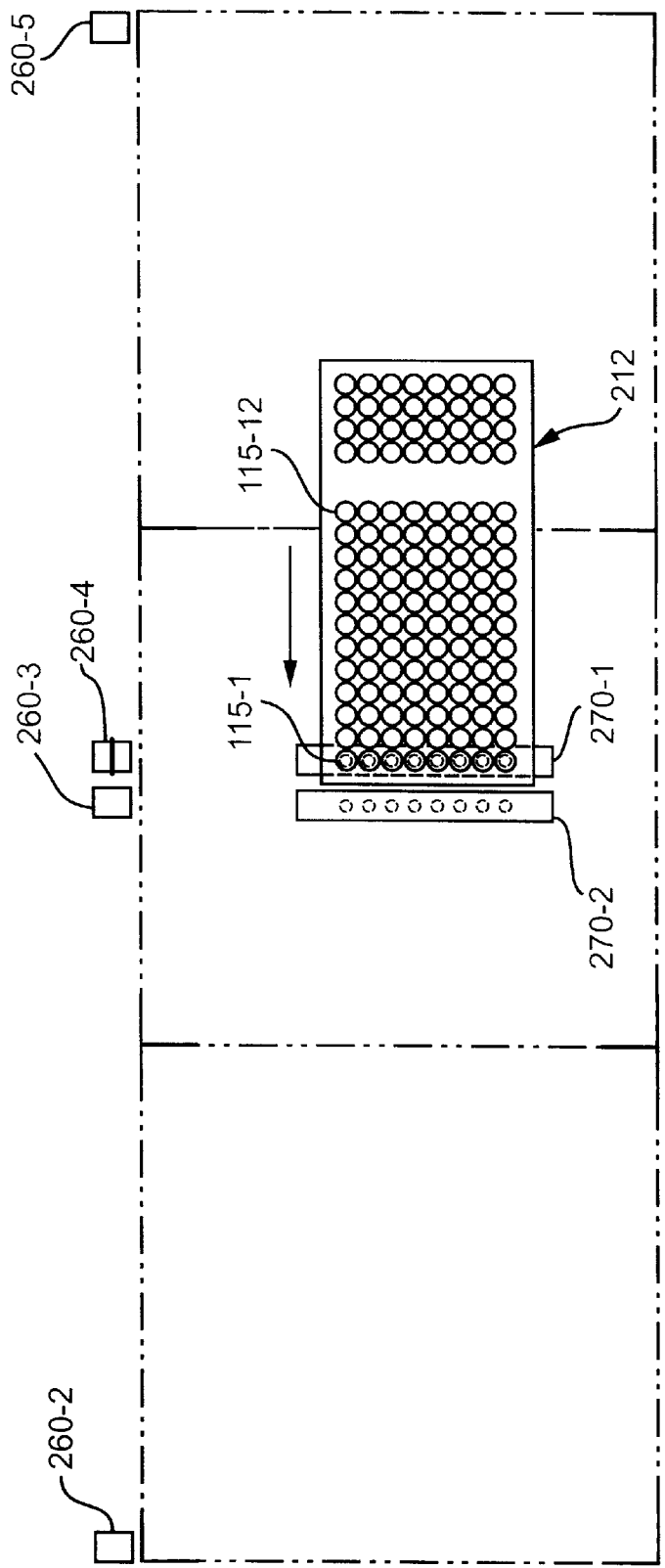
FIG. 21 is a diagram illustrating the relationship between the first column of microwells of the microwell array, housed in the stage, and one of the light sensor bars of the apparatus shown in FIG. 5 when that column of microwells is being read by one of the light sensor bars.

The microcontroller 310 begins the well read operation in step 1900. Before the microcontroller 310 controls the stepper motor 220 to convey the stage 212 to be aligned with respect to the light sensor bar which will perform the readings in step 1910, the microcontroller 310 will maintain the stage 212 at the home position as shown in FIG. 20 for a predetermined period of time (60 seconds in this embodiment).

Figure 22:
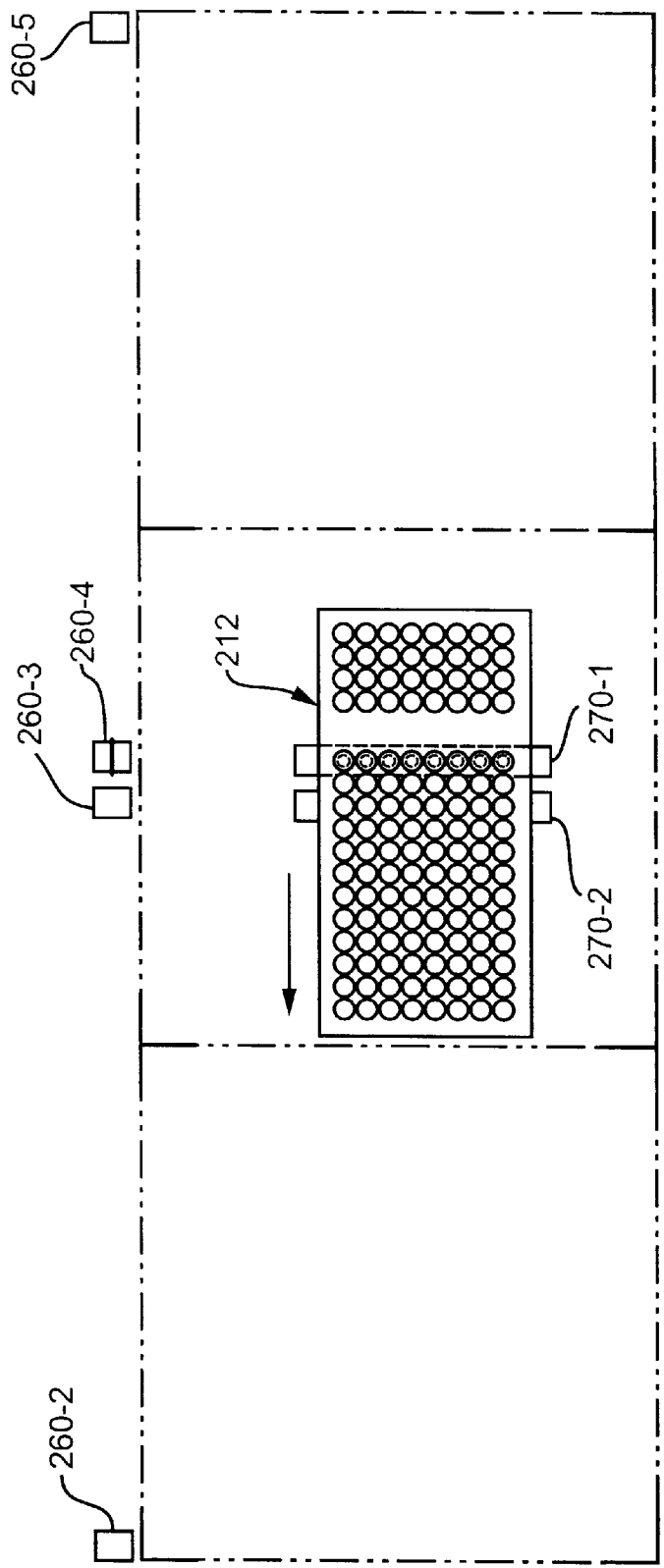
FIG. 22 is a diagram showing the relationship between the last column of microwells, of the microwell array housed in the stage, and a light sensor bar of the apparatus shown in FIG. 5 when the light sensor bar is reading the last column of microwells.

In step 1920, the microcontroller 310 then controls the stepper motor 220 to convey the stage 212 in the direction toward the first light bar sensor 270-1 at a predetermined speed until the flag 258-12 corresponding to the first column 115-1 of wells 116 in the well array 112 is detected by sensor 260-4. In step 1930, the microcontroller 310 then controls the stepper motor 220 to move the carriage the appropriate number of steps so that the centers of the wells in the column are positioned directly above the light emitting/detecting ports 284-1 through 284-8 as shown in FIG. 22. It is noted that this optimum number of steps has been determined in the well mapping procedure discussed above with reference to FIG. 13. The microcontroller 310 will then stop the stepper motor 220 from conveying the stage 212 for a brief period of time in step 1940 to allow the fluid samples in the wells 116 to settle.

In step 1950, the microcontroller 310 will prepare to energize the first LED 275-1 corresponding to the first well 116-1 in column 115-1. The microcontroller 310 will then energize the LED 275-1 so that the LED will transmit light through optical cable 280-1 and out the light emitting/detecting port 272-1 into the corresponding well in step 1960, and the microcontroller 310 will control the photomultiplier tube light detector 276-1 to detect the light being emitted from the well in response to the irradiated light. In step 1970, the microcontroller 310 will store the reading, and the process will repeat until 100 readings have been taken of the well 116-1 as determined in step 1980. It is noted that the LED 275-1 need only be energized one time for the 100 readings to be taken. Furthermore, the number of readings need not be 100, but can be 150 or any practical number, as desired.

After the 100 readings have been stored, the microcontroller 310 averages those 100 readings in step 1990 and stores the average value of the readings. The microcontroller then prepares to energize the next LED 275-2 in step 2000 so that readings can be taken from the second well 116-1 in the column 115-1 and the above steps 1960–2000 until the microcontroller determines in step 2010 that all eight wells in the column 115-1 have been read. It is further noted that if the microcontroller 310 has determined in the calibration steps described above that some of the LEDs are malfunctioning, the wells corresponding to those LEDs will not be read. Hence, in a column including 8 wells, the maximum amount of wells that could be read is all 8, and the minimum could be as low as only one.

When the microcontroller determines in step 2010 that all wells in the column have been read, the microcontroller will determine in step 2020 whether all of the columns 115-1 through 115-12 have been read. If all of the columns have not been read, the processing will return to step 1920 where the microcontroller 310 will control the stepper motor 220 to center the next column 115-2 of wells 116 over the light emitting/detecting ports 272-1 through 272-8. This centering is achieved by the microcontroller 310 controlling the stepper motor 220 to convey the stage 212 until the next flag 258-2 is detected by sensor 260-3. The stepper motor is then controlled to move the stage the necessary number of times (steps) so that the centers of the wells 116 in the second column 115-2 of wells are directly over light emitting/ detecting ports 272-1 through 272-8. The microcontroller then energizes the LEDs 275-1 through 275-8 in the manner described above in steps 2050 through 2110, and the 100 readings for each well are taken, averaged and stored until all 8 wells in that second column 115-2 have been read.

This processing will continue until the stage has been moved to read the last column 215-12 of wells 116, as shown in FIG. 22, and microcontroller 310 determines in step 2120 that all of the columns (e.g., 12) have been read. The microcontroller 310 will control the stepper motor 220 to convey the stage 212 to read those calibration wells 215-1 through 215-4 for performing the calibration associated with the light sensor bar 270-1 as described above. The microcontroller then energizes the LEDs 275-1 through 275-8 and detection 276-1 to read the calibration microwells 116C in those columns in the manner described above. This is done so that the read valves from the calibration wells can be used to adjust the read valves from the sample wells 116, if necessary, to compensate for any detector, LEDs, and so on, due to, for example, the heating of the PMT detector 276-1, changes in ambient temperature, and the like.

Figure 23:
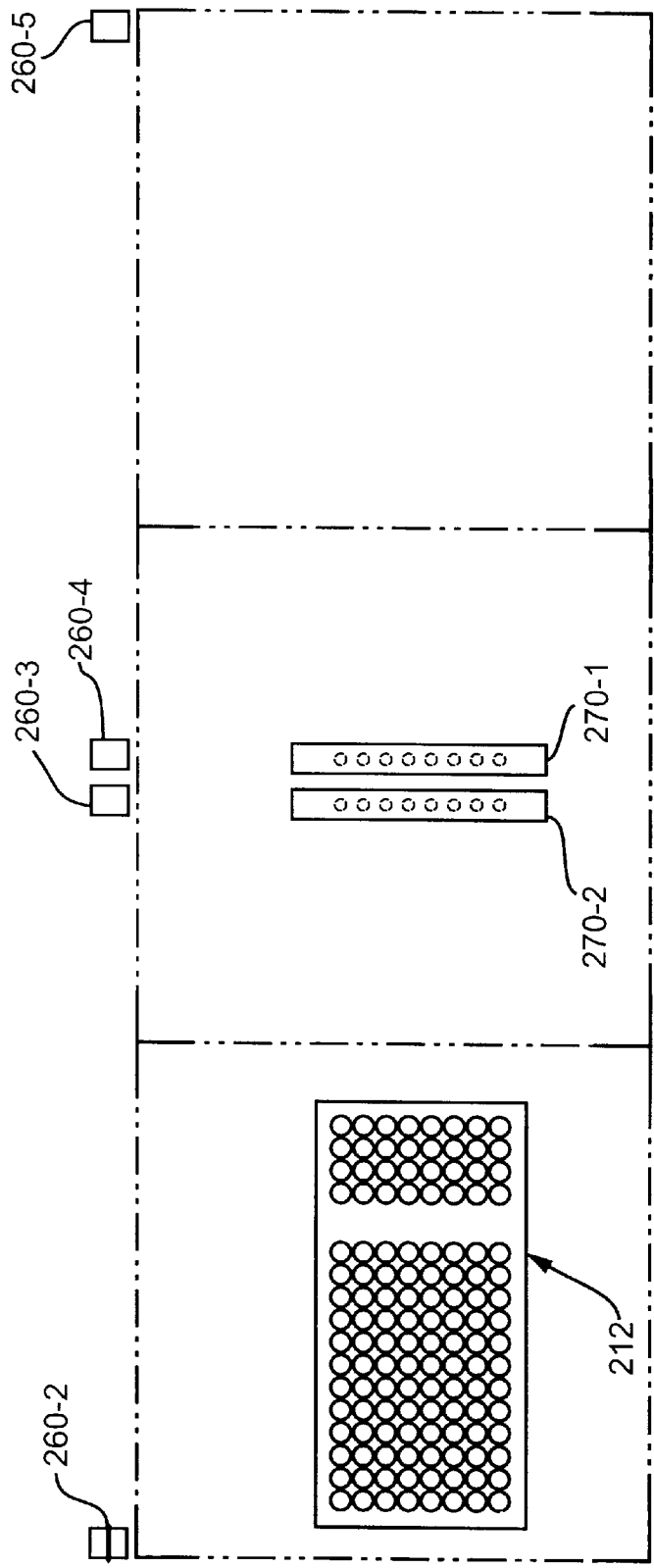
FIG. 23 is a diagram showing the relationship between the microwell array, housed in the stage, and the light sensor bars of the apparatus shown in FIG. 5, when the stage is positioned at the leftmost position in the stage assembly.

After reading the calibration columns, the microcontroller will proceed to step 2030, where it will control the stepper motor 220 to convey the stage 212 to the position along rail 218 corresponding to sensor 260-2 (the left sensor), as shown in FIG. 23. The microcontroller 310 will then control the stepper motor 220 in step 2040 to convey the stage 212 at a high speed back to the home position corresponding to the location of sensor 260-5. This processing from steps 1920 through 2040 takes approximately 1 minute. If the microcomputer determines in step 2050 that an entire test run has been completed, the processing will terminate in step 2060. However, in this embodiment, the above processing is repeated 60 times in a test run, which takes approximately one hour to complete (approximately one minute per test run). Hence, after completing one reading of all of the wells 116 in the well array 112, the processing beginning at step 2010 described above will be repeated another 59 times until a total of 60 average readings for each well have been calculated and stored.

It is further noted that the second light bar sensor 270-2 can be used to perform a second reading of the wells 116 in the well array 112. That is, as described above, each well array 112 can contain two detection probes for detecting two different types of target DNA. Alternatively, certain wells can include one type of detection probe, and other wells can include another type of detection probe. In that event, the microcontroller 310 is programmed by the operator to read some of the wells with the first light bar 270-1, and the other wells with the second light bar 270-2.

Figure 24:
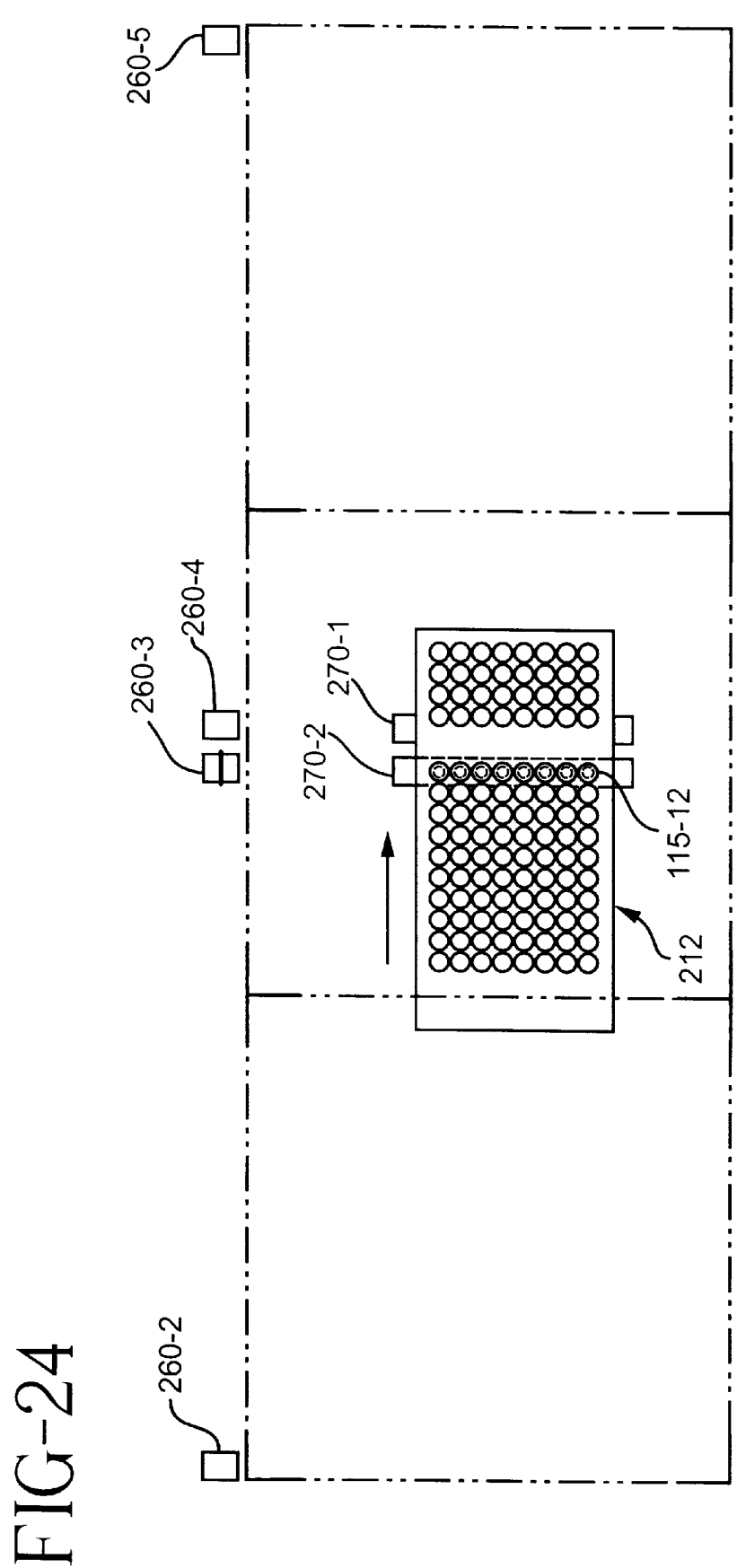
FIG. 24 is a diagram showing the relationship between the last column of microwells of the microwell array, housed in the stage, and the other light bar sensor of the apparatus shown in FIG. 5 when that light sensor bar is reading the last column of microwells.
Figure 25:
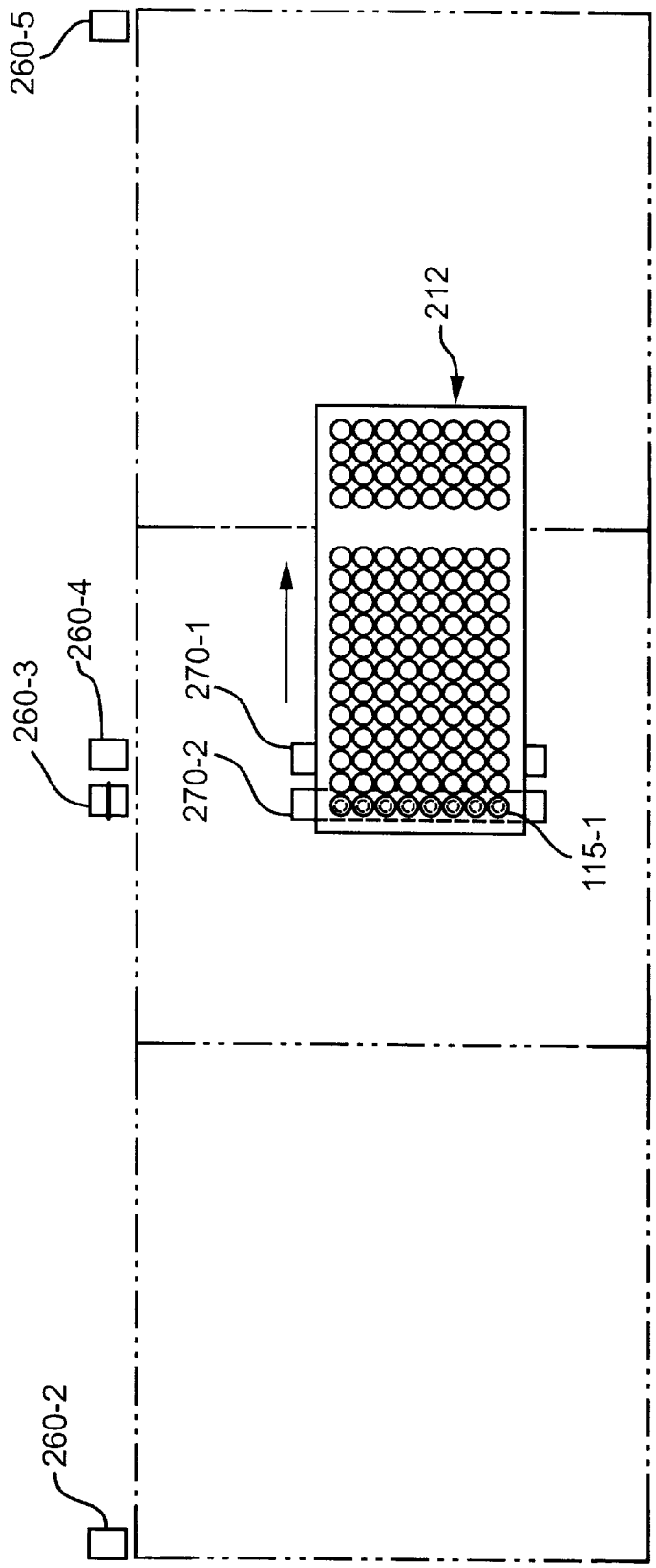
FIG. 25 is a diagram illustrating the relationship between the first column of microwells of the microwell array, housed in the stage, and the other light bar sensor of the apparatus shown in FIG. 5 when that light sensor bar is reading the first column of microwells.

In either event, the second reading can be performed by the second light bar 270-2 when the tray 212 is being conveyed from the position of the left sensor 260-2 back to the position of the home sensor 260-5 when this second reading is to be performed, the microcontroller 310 will not return the stage 212 directly to the home position in step 2040. Rather, the microcomputer 310 will control the stepper motor, the LEDs and the photodetector to operate in precisely the same manner as described above with regard to steps 2010 through 2160. However, the stepper motor will convey the stage 212 in the opposite direction as illustrated in FIG. 24 until the sensor 260-3 associated with the second light bar 270-2 detects the presence of the flag corresponding to the calibration column for performing calibration with regard to the second light bar sensor 270-2 as described above. The calibration columns well be read and then the stage 212 will be conveyed until the flag 258-12 corresponding to the first column of wells 215-12 on the right hand side of the stage 212 is detected by sensor 260-3. Those wells will be centered above the light emitting/detecting ports 272-1 through 272-8 of the second light sensor bar 270-2 in the manner described above, and the LEDs 275-1 through 275-8 of the second LED array 274-2, and the light detector 276-2 will be controlled accordingly to take the 100 readings for each well. The columns will then be scanned on a column by column basis, until all of the columns have been sensed as detected in step 2120, in which event the stage 212 is positioned as in FIG. 25. The microcontroller 310 then controls the stepper motor 220 to return stage 212 directly to the home position at sensor 260-5. For efficiency, the reading by the first light bar sensor 270-1 and second light bar sensor 270-2 will be completed within the 60 second cycle. Therefore, after one hour, 60 reads by the first light sensor 270-1, and 60 reads by the second light sensor 270-2, have been completed.

It is also noted that instead of centering the wells in step 2030, a "Fly by" reading of the wells in each column can be taken. This fly by reading would be performed as is the calibration readings described above to produce a bell shaped curve reading as shown in FIG. 14 for each well in the column. The maximum points of these readings can be stored for each well.

After an entire run has been completed for each of the light bars 270-1 and 270-2, the microcontroller 310 can control the display 204 to display the results of the test. Alternatively, the results can be printed out on a printer (not shown), or stored on a disk. If another array 112 of wells 116 is to be tested, the preliminary steps are performed on that array of wells as described above with respect to FIGS. 1–3, and the apparatus 107 is operated to perform the processing discussed above for that new well array.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. An apparatus for analyzing a plurality of samples, comprising:

a plurality of light emitting devices which are each controlled to radiate excitation light toward a respective one of the plurality of samples at respective different times to excite the samples to generate emission light at emission times corresponding to the respective different times;

a light detector which is controlled to detect the emission light emitted from the plurality of samples at the emission times; and a plurality of bifurcated light conducting devices, each comprising first and second light conducting devices each having first and second light ends, the first ends of the first and second light conducting devices being integrated with each other to form an integrated end;

the second end of the first light conducting device of each of the bifurcated light conducting devices being configured to receive the excitation light from a respective light emitting device, such that the excitation light is transmitted through the first light conducting device and output from the integrated end.

2. An apparatus as claimed in claim 1, further comprising:
a plurality of light emitting/detecting ports, each of which is optically coupled to a respective one of the plurality of light emitting devices to emit the excitation light emitted by the respective light emitting device toward a respective one of the plurality of samples, and is configured to receive the emission light from the respective sample.

3. An apparatus as claimed in claim 2, further comprising:
a sample housing device, configured to accommodate the plurality of samples and being movable to position the plurality of samples in relation to the plurality of light emitting/detecting ports such that each of the plurality of samples is positioned to receive the excitation light from its respective light emitting/detecting port.

4. An apparatus as claimed in claim 3, wherein
the sample housing device is configured to arrange the plurality of samples into a plurality of columns with each of said columns including a plurality of said samples; and
the sample housing device is movable to position each of said columns at a first position at different times, such that when a said column is at said first position, its samples are positioned to receive the excitation light from their respective light emitting devices.

5. An apparatus as claimed in claim 3, further comprising a sample mapping device for locating the positions of the samples in the sample housing device.

6. An apparatus as claimed in claim 3, further comprising:
a controller, adaptable to control the sample housing device to maintain the plurality of samples stationary when the plurality of samples are receiving the excitation light from their respective light emitting/ detecting ports.

7. An apparatus as claimed in claim 3, further comprising a controller which is adaptable to:
control the sample housing device to move incrementally such that each of the plurality of samples moves incrementally in relation to its respective light emitting/ detecting port; and
for each incremental movement of the sample housing device, control each of the plurality of light emitting devices to radiate excitation light toward its respective sample and control the light detector to detect the emission light emitted from the samples.

8. An apparatus as claimed in claim 5, wherein the sample mapping device:
controls the sample housing device to move incrementally such that each of the plurality of samples moves incrementally in relation to its respective light emitting/ detecting port; and
for each incremental movement of the sample housing device, controls each of the plurality of light emitting devices to radiate excitation light toward its respective sample while controlling the light detector to detect the emission light emitted from the samples and provide incremental light detection information.

9. An apparatus as claimed in claim 8, wherein:
the sample mapping device further comprises a position calculator, adaptable to calculate the locations of the samples in the sample housing device based on the incremental light detection information.

10. An apparatus as claimed in claim 1 wherein
the second ends of the second light conducting devices are integrated to form a detection end;
the integrated end of each of the bifurcated light conducting devices are configured to receive the emission light emitted from a respective one of the plurality of samples, such that the emission light is transmitted through the second light conducting device and output from the detection end to the light detector.

11. An apparatus as claimed in claim 1, further comprising:
a controller which is adaptable to adjust the detecting sensitivity of the light detector based on information provided by the light detector indicative of the detected emission light.

12. An apparatus for analyzing a plurality of samples, comprising:
a plurality of light emitting devices which are each controlled to radiate excitation light toward a respective one of the plurality of samples at respective different times to excite the samples to generate emission light at emission times corresponding to the respective different times;
a light detector which is controlled to detect the emission light emitted from the plurality of samples at the emission times;
a plurality of second light emitting devices which are each controlled to radiate excitation light toward a respective one of a second plurality of second samples at respective different second times to excite the second samples to generate emission light at second emission times corresponding to the respective different second times; and
a second light detector which is controlled to detect the emission light emitted from the plurality of second samples at the second emission times; and
wherein one of the following conditions is met:
all of the first samples are different from all of the second samples; or
at least some of the first and second samples are the same samples.

13. A method for analyzing a plurality of samples, comprising:
controlling a plurality of light emitting devices to radiate excitation light toward a respective one of the plurality of samples at respective different times to excite the samples to generate emission light at emission times corresponding to the respective different times;
controlling a detector to detect the emission light emitted from the plurality of samples at the emission times;
controlling a plurality of second light emitting devices to radiate excitation light toward a respective one of a second plurality of second samples at respective different second times to excite the second samples to generate emission light at second emission times corresponding to the respective different second times; and
controlling a second light detector to detect the emission light emitted from the plurality of second samples at the second emission times; and
wherein one of the following conditions is met:
all of the first samples are different from all of the second samples; or
at least some of the first and second samples are the same samples.

14. A method as claimed in claim 13, wherein:

the light emitting device controlling step comprises the step of directing the excitation light emitted by each of the light emitting devices through a respective one of a plurality of light emitting/detecting ports toward a respective said sample; and the detector controlling step comprises the steps of:
receiving the emission light emitted by each of the plurality of samples through a respective one of the light emitting/detecting ports; and
directing the received emission light to the detector.

15. A method as claimed in claim 14, further comprising the steps of:

arranging the plurality of samples in a sample housing device; and moving the sample housing device to position the plurality of samples in relation to the plurality of light emitting/detecting ports such that each of the plurality of samples is positioned to receive the excitation light from its respective light emitting/detecting port.

16. A method as claimed in claim 15, wherein the arranging step comprises the step of arranging the plurality of samples in the sample housing device into a plurality of columns with each of said columns including a plurality of said samples; and the method further comprises the step of:
moving the sample housing device to position each of said columns at a first position at different times, such that when a said column is at said first position, its samples are positioned to receive the excitation light from their respective light emitting devices.

17. A method as claimed in claim 13, further comprising:

controlling the sample housing device to move incrementally such that each of the plurality of samples moves incrementally in relation to its respective light emitting/detecting port; and for each incremental movement of the sample housing device, controlling each of the plurality of light emitting devices to radiate excitation light toward its respective sample while controlling the light detector to detect the emission light emitted from the samples, and providing incremental light detection information.

18. A method as claimed in claim 17, further comprising the step of:

calculating the locations of the samples in the sample housing device based on the incremental light detection information.

19. A method as claimed in claim 13, further comprising:

controlling the sample housing device to maintain the plurality of samples stationary when the plurality of samples are receiving the excitation light from their respective light emitting/detecting ports.

20. A method as claimed in claim 13, further comprising the steps of:

adjusting the detecting sensitivity of the light detector based on information provided by the light detector indicative of the detected emission light.

21. An apparatus for optically scanning a plurality of samples, comprising:

a sample housing apparatus, comprising a heating element for heating said samples;

a light scanning apparatus for optically scanning said samples;

a conveying apparatus which conveys the sample housing apparatus to the light scanning apparatus;

a base to accommodate said samples; and a lid to cover a side of the samples opposite to a side of the samples from which the samples are optically scanned;

wherein one of the base and the lid comprises a latching member, wherein the latching means comprises a magnet which magnetically secures the lif to the base to releasably secure the lid to the base.

22. An apparatus for analyzing a plurality of samples, comprising:

a plurality of light emitting devices which are each controlled to radiate excitation light toward a respective one of the plurality of samples at respective different times to excite the samples to generate emission light at emission times corresponding to the respective different times;

a light detector which is controlled to detect the emission light emitted from the plurality of samples at the emission times; and a controller which is adaptable to control the light detector to detect the presence of light when the plurality of light emitting devices are off, and which provides a signal indicative of light detection when the light detector detects the presence of light.

23. A method for analyzing a plurality of samples, comprising:

controlling a plurality of light emitting devices to radiate excitation light toward a respective one of the plurality of samples at respective different times to excite the samples to generate emission light at emission times corresponding to the respective different times;

controlling a detector to detect the emission light emitted from the plurality of samples at the emission times;

controlling the light detector to detect the presence of light when the plurality of light emitting devices are off; and providing a signal indicative of light detection when the light detector detects the presence of light.

24. A method for optically scanning a plurality of samples, comprising:

accommodating said samples in a sample housing apparatus which heats said samples;

conveying said sample housing apparatus past an optical scanning device which optically scans said samples;

providing a lid on the sample housing apparatus to cover a side of the samples opposite to a side of the samples from which the samples are optically scanned; and releasably magnetically securing the lid to the sample housing apparatus such that the lid covers the samples.

* * * * *